(12) United States Patent
Fukuchi et al.

(10) Patent No.: US 7,270,972 B1
(45) Date of Patent: Sep. 18, 2007

(54) PROCESS FOR PRODUCING SUBUNIT PEPTIDE ORIGINATING IN POLYMER PROTEIN

(75) Inventors: Naoyuki Fukuchi, Kawasaki (JP); Shunsuke Kageyama, Kawasaki (JP); Morikazu Kito, Kawasaki (JP); Takashi Kayahara, Kawasaki (JP); Hiroshi Yamamoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/926,256

(22) PCT Filed: Mar. 31, 2000

(86) PCT No.: PCT/JP00/02127

§ 371 (c)(1), (2), (4) Date: Oct. 2, 2001

(87) PCT Pub. No.: WO00/59926

PCT Pub. Date: Oct. 12, 2000

(30) Foreign Application Priority Data

Apr. 2, 1999 (JP) .............................. 11/096073

(51) Int. Cl.
*C12Q 1/56* (2006.01)
*A61K 38/00* (2006.01)

(52) U.S. Cl. ........................ 435/13; 514/2; 530/300
(58) Field of Classification Search ............... None
See application file for complete search history.

(56) References Cited

U.S. PATENT DOCUMENTS

| 4,847,325 | A | * | 7/1989 | Shadle et al. ............... 525/54.1 |
| 5,206,344 | A | | 4/1993 | Katre et al. |
| 5,856,126 | A | | 1/1999 | Fukuchi et al. |

FOREIGN PATENT DOCUMENTS

| EP | 0 539 167 | 4/1993 |
| JP | 61-12630 | 1/1986 |
| JP | 64-66213 | 3/1989 |
| JP | 1-279898 | 11/1989 |
| JP | 6-504765 | 6/1994 |
| WO | WO92/16221 | 10/1992 |
| WO | WO94/12219 | 6/1994 |
| WO | WO95/08573 | 3/1995 |
| WO | WO95/32003 | 11/1995 |
| WO | WO99/64460 | 12/1999 |

OTHER PUBLICATIONS

Woghiren et al. Bioconjugate Chem. 4: 314-318 (1993). Protected Thiol-Polyethylene Glycol: A New Activated Polymer for Reversible Protein Modification.*
Deng et al. Biochem Biophys Res Commun 228(2): 557-566 (1996).*
Rowlett et al., "Mutations in the contact region between the alpha and beta subunits of tryptophan synthase alter subunit interaction and intersubunit communication", Biochemistry 37: 2961-2968 (1998).*
Perutz et al., "The stereochemical mechanism of the cooperative effects in hemoglobin revisited", Annu. Rev. Biophys. Biomol. Structure 27: 1-34 (1998).*
Basu et al., "Structure-function engineering of interferon-beta-1b for improving stability, solubility, potency, immunogenicity, and pharmacokinetic properties by site-selective mono-pegylation", Bioconjugate Chem. 17: 618-630 (2006).*
J. L. Cleland, et al., The Journal of Biological Chemistry, vol. 267, No. 19, pp. 13327-13334, XP-000676508, "Polyethylene Glycol Enhanced Refolding of Bovine Carbonic Anhydrase B", 1992.

* cited by examiner

*Primary Examiner*—Robert A. Wax
*Assistant Examiner*—Anand Desai
(74) *Attorney, Agent, or Firm*—Oblon, Spivak, McClelland, Maier & Neustadt, P.C.

(57) ABSTRACT

It is provided a method for producing a subunit peptide originating from an oligomeric protein having disulfide bonds within a subunit and between subunits. The method comprises producing a subunit originating from an oligomeric protein having disulfide bonds within a subunit and between subunits by the following steps:
(a) a step of refolding the subunit by denaturing the oligomeric protein or its subunit in a solution with a protein-denaturing agent and removing the denaturing agent from the solution in the presence of polyoxyalkyl polyether having a functional group that reacts with a thiol group; and
(b) a step of isolating the subunit bonded to the polyoxyalkyl polyether from the solution.

8 Claims, 8 Drawing Sheets

FIG. 6a
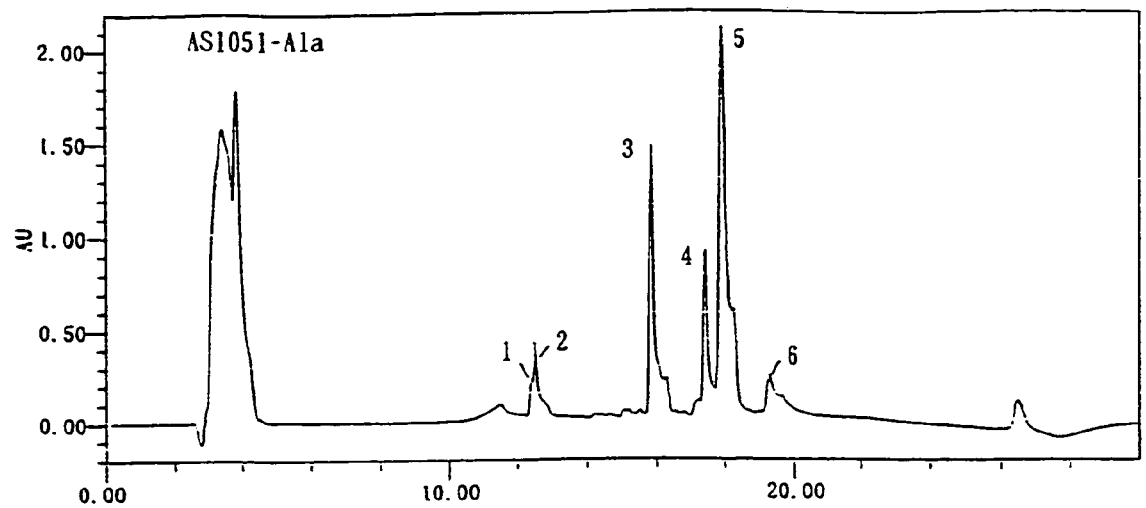
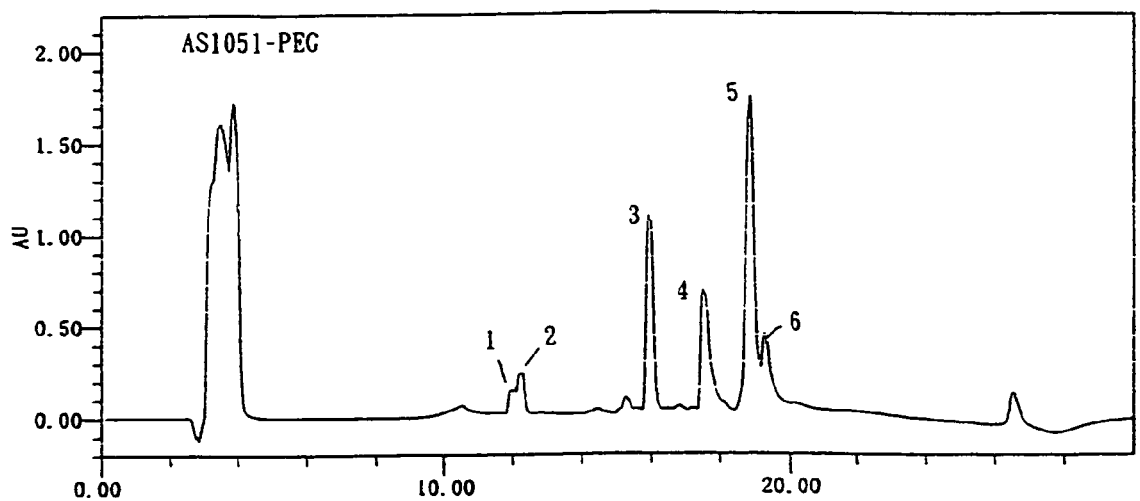
1 PFK
2 FTRPR
3 DLECPSGWSSYDRYCYK
4 EYLTRYIWIGLRVQNK
5 QEMTWADAERFCSEQAK
　VDCEQQHSFICK
　GQPXSSISYENLVDPFECFMVSRDTRLREWFK
　　X=Ala or Cys-PEG
6 GGHLLSVETALEASFVDNVLYANK
FIG. 6b AS1051-Ala

AS1051-PEG

Inhibition of restocetin-induced vWF binding

Inhibition of botrocetin-induced vWF binding

PROCESS FOR PRODUCING SUBUNIT PEPTIDE ORIGINATING IN POLYMER PROTEIN

CROSS-REFERENCE TO RELATED APPLICATIONS

The present application is a National Stage (371) of PCT/JP00/02127, filed on Mar. 31, 2000, which claims priority to JP 11/96073, filed on Apr. 2, 1999.

TECHNICAL FIELD

The present invention relates to a method for producing a subunit peptide originating from an oligomeric protein that has disulfide bonds in a subunit and between subunits, and a subunit peptide produced by this method.

BACKGROUND ART

Life activities of organisms require proteins having various physiological activities. Many of these physiologically active proteins have a disulfide bond in their molecules. Also, they exist as oligomers such as dimers composed of homogenous or heterogeneous peptide chains and are biosynthesized in a state that a disulfide bond is formed between the peptide chains. While existence as a dimer is essential for many physiologically active proteins existing as a dimer to express their biological activity, proteins that are not necessarily required to exist as a dimer are also known.

As examples of proteins that are essentially required to be a dimer to express their physiological activity, a platelet-derived growth factor (PDGF) and so forth can be mentioned. Since each peptide chain of its dimer must be bonded to each peptide chain of a receptor, which is also a dimer, it is substantially essential for the protein to be a dimer to express its physiological activity (C. H. Heldin et al., Cell. Regul., 1, pp. 555-566, 1990).

However, it is also known that, in some physiologically active dimer proteins, one peptide chain (subunit) is considered to be responsible for an activity of binding to a receptor, enzymatic activity and so forth, while the other peptide chain is considered to be important for stability, solubility, biosynthesis process and so forth of the protein. That is, only a single subunit is essential for expression of substantial physiological activity. For example, although activin exists as a homodimer or a heterodimer in a living body, it has been reported that activin still has an activity of binding to its receptor and maintains about several percents of its biological activity even when it exists as a monomer (P. Husken-Hindi et al., J. Biol. Chem., 269, pp. 19380-19384, 1994). It has also been reported that prothoracicotropic hormone (PTTH), which exists in insects and has a physiological effect, exists in a living body as a homodimer, but about 50% of its biological activity is maintained in its monomer (J. Ishibashi et al., Biochemistry, 33, pp. 5912-5919, 1994). Further, although immunoglobulin G (IgG) is also a dimer, it is known that its antigen binding property is maintained in its monomer (G. M. Edelman, Biochemistry, 7, p. 1950, 1968).

As described above, some dimer proteins exhibiting physiological activities in a living body have their physiological activities even when they exist as a monomer. Further, monomers of some dimer proteins are bound to their receptors even though the proteins do not exhibit physiological activities when they exist as a monomer. Therefore, it is considered that, if a protein existing as a dimer is obtained as a monomer, the protein can be utilized as a protein having a physiological action or as a protein for inhibiting a physiological action of an original physiologically active protein by binding to its receptor to inhibit binding of the original physiologically active protein even though it does not have the physiological action.

Further, there are known many cases where proteins produced by different animal species exhibit a physiological activity in other animal species. For example, it is known that hirudin, which is a protein isolated from leech saliva, is bound to thrombin, which is a coagulation factor in blood, and thereby inhibits its protease activity. Proteins such as disintegrin and CHH-B that are bound to a platelet receptor and thereby inhibit platelet aggregation, are also known as proteins originating from snake venom. Among such heterogeneous proteins, CHH-B is a protein that is bound to glycoprotein Ib (GPIb), which is a glycoprotein on a platelet membrane, and thereby inhibits platelet aggregation. It has been reported that CHH-B is a heterodimer and its monomer also maintains its GPIb-binding activity and platelet aggregation inhibitory activity equally compared to those of the heterodimer (N. Fukuchi et al., WO 95/08573).

That is, it is considered that such a monomer of a physiologically active protein biosynthesized as a dimer as described above can be utilized as an action protein (agonist) or an action inhibitory protein (antagonist), and would be useful as a therapeutic agent for various diseases.

However, there are two major problems in obtaining a protein that is originally biosynthesized and exists as a dimer in a living body, in a form of a monomer in which its three-dimensional structure is maintained to such an extent that it should be stable and exhibit at least its biological activity.

The first problem is that preparation of a monomer is difficult. Two major methods are widely used to obtain a protein as a monomer that originally exists as a dimer. In one method, a dimer protein is partially reduced to cleave only a disulfide bond between subunits and then a newly generated free thiol groups are blocked. In the other method, a cysteine residue involved in a disulfide bond between subunits is replaced with an alanine residue or a serine residue by a technique of molecular biology and then a monomer is produced by using a protein synthesis system using an animal cell or the like. As for the aforementioned proteins, the former method is used for PTTH, CHH-B and IgG, while the latter method is used for activin and CHH-B. In the former method, since it is difficult to determine conditions for cleaving only the disulfide bond between subunits in some proteins, there have been few cases where a monomer was obtained while maintaining the activity. In the latter method, since the cysteine residue involved in the disulfide bond between subunits must be identified in advance and then a point mutation must be further inserted into the obtained gene. Therefore, it is a complicated method.

The second problem is that antigenicity may be expressed. When a protein existing as a dimer in a living body is obtained as a monomer, antigenicity may be exhibited because a region originally existing inside the molecule is exposed outside and may be recognized as a heterogeneous protein. In addition to this, in the first method for preparing a monomer, in which thiol groups are blocked after reduction, a compound used for blocking may exhibit antigenicity. Further, in the second method, in which a mutation is inserted, a partial structure containing the mutated amino acid may also exhibit antigenicity. Further, a protein originating from different animal species generally has antigenicity, and a protein obtained as a monomer also has a similar problem of antigenicity expression.

Meanwhile, it is well known that antigenicity of a protein can be decreased by polyethylene-glycolating (Bioconjugate Drugs, Drug Development, continued, Special Issue, Ed. by Inada and Tanimoto, Hirokawa Shoten, 1993; A. Abuchowski et al., J. Biol. Chem., 252, pp. 3578-3581, 1997). In particular, there have also been many reports on methods using polyethylene glycol having a functional group that is bound to a free thiol group of a cysteine residue in order to limit the number of polyethylene glycol molecules bound to a protein and their binding positions (G. N. Cox et al., WO98/32003; G. N. Cox et al., WO94/12219; R. J. Goodson, U.S. Pat. No. 5,206,344; L. G. Armes, WO92/16221). However, in all of these methods, a cysteine residue is artificially inserted in a part of a protein or replaced. There have been no reports that a useful protein is obtained by binding polyethylene glycol to a free thiol group without artificially replacing an amino acid in a subunit that originally forms a dimer.

DISCLOSURE OF THE INVENTION

The present invention was accomplished in view of the aforementioned problems, and an object thereof is to provide a method for easily obtaining, as a monomer, a subunit having a biological activity in a protein that originally exists as an oligomer such as a dimer and simultaneously decreasing its antigenicity.

The inventors of the present invention assiduously studied in order to achieve the aforementioned object. As a result, they found that, when a subunit constituting an oligomeric protein was refolded by denaturing the subunit with a protein-denaturing agent and then removing the denaturing agent, if the subunit was refolded in the presence of polyethylene glycol having a functional group that could bond to a cysteine residue, a monomer peptide maintaining an original activity of the subunit and having decreased antigenicity could be obtained. Thus, they accomplished the present invention.

The present invention provides the followings.

(1) A method for producing a subunit peptide originating from an oligomeric protein having disulfide bonds within a subunit and between subunits, which comprises the following steps:

(a) a step of refolding the subunit peptide by denaturing the oligomeric protein or its subunit peptide in a solution with a protein-denaturing agent and removing the denaturing agent from the solution in the presence of polyoxyalkyl polyether having a functional group that reacts with a thiol group; and (b) a step of isolating the subunit peptide bonded to the polyoxyalkyl polyether from the solution.

(2) The method according to (1), wherein the subunit peptide isolated in step (b) has decreased antigenicity.

(3) The method according to (1), wherein the oligomeric protein is a dimer.

(4) The method according to (1), wherein the polyoxyalkyl polyether having the functional group that reacts with the thiol group is polyethylene glycol having a maleimide group.

(5) The method according to (1), wherein the subunit peptide originating from the oligomeric protein is a recombinant protein.

(6) The method according to (1), wherein the oligomeric protein or its subunit peptide is denatured under reducing conditions.

(7) The method according to (1), wherein a physiological activity of the oligomeric protein arises from a subunit peptide constituting the oligomeric protein, and the subunit peptide bonded to polyoxyalkyl polyether has the physiological activity.

(8) The method according to (1), wherein the subunit peptide bonded to polyoxyalkyl polyether has an activity of inhibiting a physiological activity of the oligomeric protein.

(9) The method according to (1), wherein the polyoxyalkyl polyether is bonded to a cysteine residue that is originally involved in formation of a disulfide bond between subunits in the oligomeric protein, among cysteine residues in the subunit peptide.

(10) The method according to (1), wherein the subunit peptide bonded to polyoxyalkyl polyether has a disulfide bond identical to a disulfide bond within the subunit in the oligomeric protein.

(11) A subunit peptide originating from an oligomeric protein having disulfide bonds within a subunit and between subunits, wherein polyoxyalkyl polyether is bonded to a cysteine residue that is originally involved in formation of a disulfide bond between subunits of the oligomeric protein, among cysteine residues in the subunit peptide, and the subunit peptide has decreased antigenicity.

(12) The subunit peptide according to (11), wherein the oligomeric protein is a dimer peptide that originates in snake venom and has an activity of inhibiting binding of a von Willebrand factor to a platelet.

(13) The subunit peptide according to (12), wherein the snake venom is snake venom of *Crotalus horridus horridus*.

(14) The subunit peptide according to (12), which exhibits an antithrombotic activity.

(15) The subunit peptide according to (14), which is a peptide having the amino acid sequence shown in SEQ ID NO: 1 and having polyoxyalkyl polyether bonded to the cysteine residue of amino acid number 81 in the amino acid sequence, or a derivative thereof.

BRIEF DESCRIPTION OF THE DRAWINGS

FIG. 6a is a reverse phase liquid chromatogram of the AS1051 protein in which the cysteine residue at position 81 was replaced with an alanine residue (AS1051-Ala) after digestion with lysyl endopeptidase. FIG. 6b is a reverse phase liquid chromatogram of the polyethylene-glycolated AS1051 (AS1051-PEG) after digestion with lysyl endopeptidase. The polypeptide fragments in FIG. 6 can be found in the Sequence Listing as follows: sequence 1=residues 41-43 of SEQ ID NO: 5; sequence 2=residues 145-149 of SEQ ID NO: 5; sequence 3=residues 24-40 of SEQ ID NO: 5; sequence 4 (top)=residues 85-100 of SEQ ID NO: 5 and sequence 4 (bottom)=residues 44-60 of SEQ ID NO: 5; sequence 5 (top)=residues 133-144 of SEQ ID NO: 5 and sequence 5 (bottom)=residues 101-132 of SEQ ID NO: 5; sequence 6=residues 61-84 of SEQ ID NO: 5.

BEST MODE FOR CARRYING OUT THE INVENTION

Figure 1:
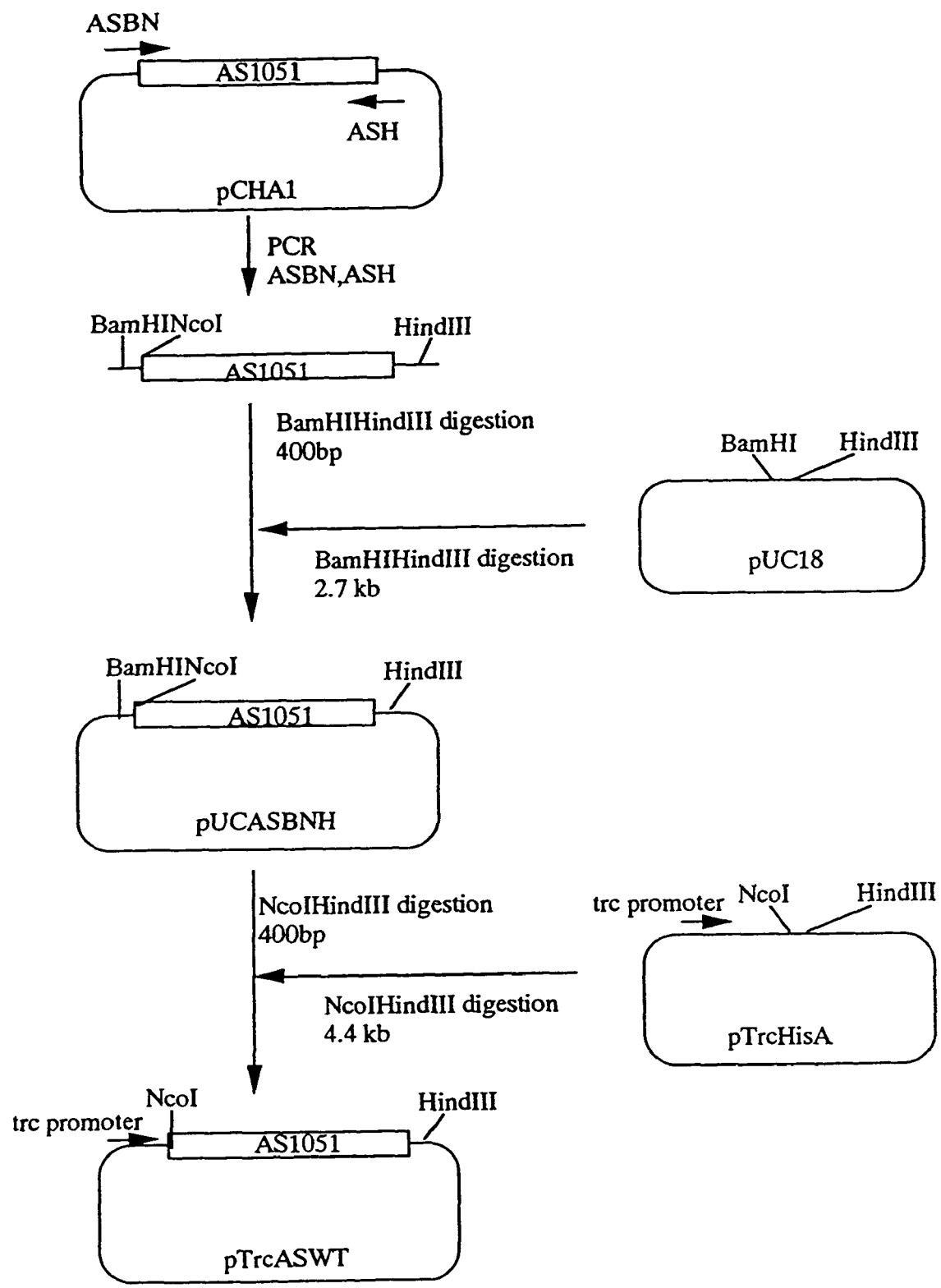
FIG. 1 shows a construction process of vector pTrcASWT which expresses wild-type AS1051 (AS1051-WT).

<1> Method for Producing Subunit Peptide of Present Invention

The method of the present invention is a method for producing a subunit peptide originating from an oligomeric protein that has disulfide bonds within a subunit and between subunits and, preferably, having decreased antigenicity.

The oligomeric protein used in the present invention is composed of two or more peptide subunits and has a disulfide bond at least in one subunit peptide chain and a disulfide bond between subunits.

Examples of the oligomeric protein include an oligomeric protein whose physiological activity depends on a subunit peptide constituting the oligomeric protein. Further, the oligomeric protein may also be an oligomeric protein whose physiological activity is inhibited by the subunit peptide bonded to polyoxyalkyl polyether obtained by the method of the present invention. For example, AS1051-PEG mentioned as an example of the subunit peptide of the present invention in the Examples has an anti-platelet action similar to that of CHH-B, which is a dimer peptide originating from snake venom, from which this subunit peptide originates. Further, the aforementioned AS1051-PEG also has an activity of binding to glycoprotein on a platelet like CHH-B, which is a dimer peptide from which the subunit originates, and thereby inhibits the binding of CHH-B. In AS1051, the platelet-reducing action which CHH-B has is markedly decreased. However, even though its characteristic is changed in such a way, such a subunit peptide is not excluded so long as the aimed physiological activity is maintained.

The method of the present invention is a method for obtaining, among such subunit peptides constituting oligomeric proteins as described above, a subunit peptide having a disulfide bond within the peptide chain, which has the aforementioned physiological activity or an activity of inhibiting the physiological activity and preferably has decreased antigenicity.

The term of "decreased antigenicity" used herein means that antigenicity of the subunit peptide obtained by the method of the present invention is decreased compared with antigenicity of a subunit peptide obtained from an oligomeric protein by a conventional method. Examples of the conventional methods include, for example, a method of obtaining a monomer by reducing an oligomeric protein with a reducing agent and then alkylating a free thiol group with an alkylating agent, a method of producing a subunit peptide as a recombinant protein wherein a cysteine residue involved in a disulfide bond between subunits is replaced with another amino acid residue, and so forth.

The oligomeric protein to which the present invention is applicable is not limited so long as it is composed of two or more peptide subunits and has a disulfide bond at least in one subunit peptide chain and a disulfide bond between the subunits. Examples thereof include oligomeric proteins having an activity of binding to glycoprotein Ib on a platelet membrane, that are contained in snake venom such as those of *Crotalus horridus horridus, Cerastes cerastes, Vipera palestinae, Echis carinatus, Trimeresurus albolabris, Trimeresurus flaboviridis, Naja haje, Naja nivea* and *Crotarus admanteus*, and physiologically active proteins such as growth factors and cytokines (R. M. Scarborough, WO92/08472).

In the method of the present invention, an oligomeric protein obtained from a natural material such as snake venom may be used as it is or a subunit peptide separated from an oligomeric protein can be used. As the subunit peptide, among subunits constituting an oligomeric protein, a subunit peptide responsible for a physiological activity of the oligomeric protein or a subunit peptide having an activity of inhibiting the physiological activity is used. The subunit peptide referred to in the present invention means such a subunit peptide unless otherwise specified. Further, the subunit peptide may be a recombinant protein produced by a genetic recombination technique by using DNA coding for it.

If the total length of the amino acid sequence of the target subunit peptide or a part thereof is known, DNA coding for the subunit peptide can be cloned in the same manner as in conventional gene cloning. For example, the target gene can be obtained by the polymerase chain reaction (PCR) method using primers prepared based on a known nucleotide sequence. It can also be obtained from a cDNA library by performing hybridization using a probe prepared in a similar manner. If the target gene is deposited at a depository, the deposited gene can be used. Further, when the whole nucleotide sequence of the gene is known, the target gene can also be chemically synthesized. When a target subunit peptide cannot be identified among subunit peptides constituting an oligomer, genes coding for the respective subunit peptides may be cloned.

The subunit peptide can be produced as a recombinant protein through a genetic recombination technique by using a gene coding for the target subunit peptide in the same manner as in a conventional method for producing a useful protein. That is, a host such as *Escherichia coli* can be transformed with a recombinant vector obtained by inserting a gene coding for the target subunit peptide into a vector including an appropriate promoter, and then the transformant can be cultured to express the gene. Examples of the host include *Escherichia coli, Bacillus subtilis*, yeast and so forth. The promoter is not limited so long as it functions in the host to be used. Examples thereof include lac, trp, tac, trc, recA, T7 (New Course of Biochemical Experiment 1, Protein VI, Synthesis and Expression, Ed. by the Japanese Biochemical Society, p. 166, Yasueda & Matsui, Tokyo Kagaku Dojin Co., Ltd., 1992), PGK, ADH1, GPD, MFα1, SUC2, PHO5, GAL1, GAL4 (New Course of Biochemical Experiment 1, Protein VI, Synthesis and Expression, Ed. by the Japanese Biochemical Society, p. 215, Sakai et al., Tokyo Kagaku Dojin Co., Ltd., 1992) and so forth.

As for the expression scheme, the target subunit peptide itself may be directly expressed or it may be expressed as a fusion protein with another protein. The subunit peptide may be accumulated as an inclusion body or a soluble type protein in microbial cells, or it may be secreted out of microbial cells. Examples of the fusion protein include fusion proteins with maltose-binding protein, glutathione S-transferase, histidine-tag (His-Tag) and so forth.

A subunit peptide originating from a protein that originally exists as an oligomer may highly possibly have a cysteine residue not involved in a disulfide bond within the subunit and have a highly hydrophobic partial structure originally associated with another subunit peptide on the surface. Therefore, it is considered that such a subunit peptide by itself often results in poor stability and solubility in a solution. The poor stability due to existence of a cysteine residue not involved in a disulfide bond within the subunit can be avoided in the same manner as in a conventional method by replacing a cysteine residue originally involved in a disulfide bond between subunits with an appropriate amino acid residue such as alanine or serine, which does not have a thiol group. However, for this purpose, a cysteine residue originally involved in a disulfide bond between subunits must be identified. Even when the cysteine residue described above is already identified, a mutation for amino acid replacement must further be introduced into a gene, and its operation is complicated.

On the other hand, according to the present invention, a gene coding for a subunit peptide can be expressed as it is. When solubility and stability are poor due to such a subunit by itself peptide, the subunit peptide may be obtained as an inclusion body or an insolubilized protein.

In the present invention, a subunit peptide is obtained from an oligomeric protein or its subunit peptide as described above by the aforementioned steps (a) and (b). Each step will be explained below.

(1) Step (a)

First, an oligomeric protein or its subunit peptide is denatured in a solution with a protein-denaturing agent. Subsequently, the denaturing agent is removed from the solution in the presence of polyoxyalkyl polyether having a functional group that reacts with a thiol group to refold the subunit peptide.

A solvent of the solution is usually water. The protein-denaturing agent is not particularly limited so long as it can reversibly denature a protein. Examples thereof include guanidine hydrochloride, urea and so forth. The protein-denaturing agent can be used at any concentration so long as the protein is dissolved. However, for example, it can be used in the range of from 1 M to a saturated concentration, preferably, from 2 M to 8 M. pH of the solution is not limited, but it is preferably in the range of from 7 to 12, in which cleavage of a disulfide bond and binding of polyethylene glycol to a thiol group, which will be explained later, readily occur. The temperature of the solution is not also particularly limited, but it is preferably in the range from 0 to 40° C. The reaction time is also appropriately selected. The denaturation may be performed under either reducing conditions or non-reducing conditions.

A disulfide bond in a oligomeric protein or a subunit peptide may be cleaved beforehand by using a reducing agent, but this is not essential. A substance containing a cysteine residue such as glutathione, a reducing agent such as dithiothreitol, an enzyme such as a protein disulfide isomerase or the like can be added before the refolding process.

When an oligomeric protein or its subunit has a disulfide bond between subunits or a disulfide bond within the subunit, which is different from the disulfide bond in the original protein, the denaturation is preferably performed under reducing conditions. In the present invention, the reducing conditions means conditions under which cleavage of a disulfide bond is promoted as in the presence of a substance containing a cysteine residue, a reducing agent, protein disulfide isomerase or the like. Since cleavage of the disulfide bond is promoted under reducing conditions, the reaction with polyoxyalkyl polyether having a functional group that reacts with a thiol group is promoted in the refolding process. When an oligomeric protein is denatured, since cleavage of a disulfide bond between subunits is promoted, it is particularly preferred that the denaturation is performed under reducing conditions.

Subsequently, the denaturing agent is removed from the solution containing the denatured subunit peptide in the presence of polyoxyalkyl polyether having a functional group that reacts with a thiol group. The denaturing agent can be removed from the solution by, for example, dialysis.

Typical examples of the functional group that reacts with a thiol group include a maleimide group (R. J. Goodson et al., Bio/Technology, 8, p. 343, 1990), orthopyridyl disulfide group (M. Yokoyama et al., Biochem. Biophys. Res. Commun., 164, p. 1234, 1989), vinylsulfone group (Shearwater Polymers Inc. Item No. M-VS-5000) and so forth. The functional group is not limited so long as it preferentially bonds to a thiol group. Examples of the polyoxyalkyl polyether include polyethylene glycol, polypropylene glycol, polyhydroxyethyl glycerol, dextran, carbohydrate polymers and so forth. The molecular weight is not particularly limited, but it is preferably in the range of from 1000 to 1,000,000, more preferably in the range of from 2000 to 50,000, in view of improvement of solubility and decrease of antigenicity of a subunit peptide to be obtained, and reactivity with a subunit peptide.

The polyoxyalkyl polyether described above may be added to the solution before or after denaturation of an oligomeric protein or its subunit peptide. It may also be added before removing the denaturing agent. Usually, it is preferred that after an oligomeric protein or its subunit peptide is denatured with a denaturing agent, the polyoxyalkyl polyether is added and the mixture is allowed to react for a certain period of time and then the denaturing agent is removed from the solution. The amount of polyoxyalkyl polyether is preferably an equimolar amount or more to the amount of the protein to be reacted.

The polyoxyalkyl polyether bonds to a cysteine residue of a subunit peptide by allowing the subunit peptide to react with polyoxyalkyl polyether having a functional group that reacts with a thiol group during or after the denaturation.

When the denaturing agent is removed from the solution as described above, refolding of the denatured subunit peptide occurs, and thus a subunit peptide having a physiological activity identical to the physiological activity of the oligomeric protein from which the subunit peptide originates or an activity of inhibiting the physiological activity can be obtained.

By performing natural oxidation (air oxidation) to form a disulfide bond within a subunit and then adding polyoxyalkyl polyether having a functional group that reacts with a thiol group before the step of removing the denaturing agent from the solution containing the denatured subunit peptide, a polyoxyalkyl polyether group can be selectively and efficiently bonded to a cysteine residue originally involved in formation of a disulfide bond between subunits of the oligomeric protein.

(2) Step (b)

The subunit peptide bonded to polyoxyalkyl polyether, which is produced as described above is isolated from the solution. This operation can be performed by a combination of operations used for conventional purification of a protein, that is, widely used chromatography techniques such as ion exchange, gel filtration or reverse phase chromatography, electrophoresis, precipitation operation such as salting out, desalting operation, concentration operation and so forth.

The aimed subunit peptide and polyoxyalkyl polyether can be separated by the above operations. When an oligomeric protein is used as a start material, the target subunit peptide and other subunit peptides can be separated. For example, a subunit peptide having decreased antigenicity in which polyoxyalkyl polyether is bonded to a cysteine residue originally involved in formation of a disulfide bond between subunits in an oligomeric protein among cysteine residues in the subunit peptide, can be separated from the other subunit peptide or peptides.

The binding position of polyoxyalkyl polyether bonded to a subunit peptide is preferably at a cysteine residue that forms a disulfide bond between subunits in the oligomeric protein. However, when the formation of the disulfide bonds is not determined, it may be such a position that the polyoxyalkyl polyether bonds to a specific thiol group, whereby the subunit peptide has an aimed activity, stably exists in a solution and preferably has decreased antigenicity. The other disulfide bond within the subunit is preferably the disulfide bond within the subunit of the original oligomeric protein. However, they can be different from them in such a degree that the subunit peptide still has a substantial physiological activity. Further, when the original disulfide bond within the subunit is not determined, it may be such a position that the subunit peptide is identifiable as a single molecule having a physiological activity and stably exists in a solution. The number of polyoxyalkyl polyether molecules to be bonded per molecule is preferably equal to the number of cysteine residues forming a disulfide bond between subunits in the original dimer protein. However, when the number is not determined, it may be such a number that the obtained polyoxyalkyl-polyetherated monomer protein has a physiological activity, is identifiable as a single molecule and stably exists in a solution.

Further, it is sufficient that antigenicity of the obtained polyoxyalkyl-polyetherated monomer subunit peptide should be substantially decreased compared with a subunit peptide that is not polyoxyalkyl-polyetherated or a subunit peptide obtained by replacing a cysteine residue forming a disulfide bond between subunits in the original oligomeric protein with another amino acid having no thiol group. When there is obtained no finding about antigenicity of a subunit peptide that is not polyoxyalkyl-polyetherated as described above, it may be such antigenicity that biological and biochemical reactions attributable to an antigen-antibody reaction do not occur when the obtained polyoxyalkyl-polyetherated subunit peptide is administered to an animal at a minimal number of times required for immunization and then administered again.

Furthermore, stability in blood of the polyoxyalkyl-polyetherated subunit peptide obtained by the present invention is expected to be improved compared with the subunit peptide not polyoxyalkyl-polyetherated.

In the Examples described later, there will be mentioned an example of the method of the present invention in which the method is applied to a subunit peptide (a subunit) constituting CHH-B which is a dimer peptide originating from snake venom of *Crotalus horridus horridus*. CHH-B bonds to glycoprotein Ib (GPIb) which is a platelet membrane glycoprotein. Glycoprotein Ib is known to be involved in thrombogenesis by bonding to von Willebrand factor (vWF) which is a protein in blood (J. P. Cean et al., J. Lab. Clin. Med., 87, pp. 586-596, 1976; K J. Clemetson et al., Thromb. Haemost., 78, pp. 266-270, 1997). Further, it has been found that a GPIb-binding site exists in the α-chain of CHH-B and it has been reported that AS1051 which is only the isolated α-chain has an antithrombotic activity (N. Fukuchi et al., WO 95/08573). N. Fukuchi et al. (WO95/08573) have reported a method including partial reduction of CHH-B and protection of a free thiol group with glutathione as a method for preparing AS1051. Further, they have also reported a method wherein the gene coding for AS1051 is cloned, a cysteine residue involved in a disulfide bond between subunits in CHH-B is identified and mutant AS1051 (AS1051-Ala) in which the cysteine residue is replaced with an alanine residue is expressed in *Escherichia coli*, and so forth.

However, the above patent specification reported the data about activity obtained by using a subunit peptide obtained by partial reduction of CHH-B or a mutant AS1051, but did not mention stability of wild-type AS1051 produced in *Escherichia coli*. Therefore, it is considered that this subunit peptide having superfluous cysteine residues not involved in a disulfide bond within a subunit would have a low stability and a low efficiency in the refolding process. Further, the specification describes about evaluation of the antithrombotic activity using animals, but does not refer to the antigenicity. Therefore, stability of AS1051 produced by using *Escherichia coli* and antigenicity of the alanine-replaced product (AS1051-Ala) which was considered to be stable, upon the administration to animals were examined first.

As a result, it was confirmed that, when AS1051 and AS1051-Ala were denatured and refolded under the same conditions, solubility of AS1051 was very low. Further, when AS1051-Ala was repetitively administered to guinea pigs, decrease of platelets was confirmed, which was considered to be attributable to its antigenicity. On the other hand, AS1051 obtained by the method of the present invention, which was polyethylene-glycolated and did not have amino acid replacement, showed a high solubility and no decrease of platelets.

<2> Peptide of Present Invention

The peptide of the present invention is a subunit peptide originating from an oligomeric protein having disulfide bonds in a subunit and between subunits, wherein polyoxyalkyl polyether is bonded to a cysteine residue originally involved in formation of a disulfide bond between subunits in the oligomeric protein among cysteine residues in the subunit peptide and the subunit peptide has decreased antigenicity. Such a subunit peptide can be obtained by, for example, the above-described method of the present invention.

Specific examples of the subunit peptide of the present invention include a subunit peptide originated from an oligomeric protein that is a dimer peptide derived form snake venom of Crotalus horridus horridus and having an activity of inhibiting binding of the von Willebrand factor to platelets. A specific example is a peptide having the amino acid sequence shown in SEQ ID NO: 1, and having polyoxyalkyl polyether bonded to the cysteine residue of the amino acid number 81 in the amino acid sequence, or a derivative thereof. Examples of the derivative include a peptide that includes replacement, deletion, insertion, addition or inversion of one or several amino acid residues at a position other than the cysteine residue of the amino acid number 81 and has an antithrombotic property.

The peptides as described above have superior characteristics, namely, an activity of inhibiting platelet aggregation similar to that of the original dimer protein, CHH-B, or its α subunit monomer peptide, AS1051, high solubility in a solution such as a buffer and very low antigenicity, while AS1051 that is not polyetherated exhibits antigenicity.

<3> Use of Peptide of Present Invention

Among subunit peptides obtained by the method of the present invention, those having substantially the same biological action as that of the original oligomeric protein, can be utilized in a drug as an active substance for the target of the action. Further, among subunit peptides obtained by the method of the present invention, for example, those having a physiological activity of inhibiting a biological action of the original oligomeric protein based on a mechanism such as inhibition of binding of the original oligomeric protein to its receptor or the like, can also be utilized in a drug as an inhibitory substance for the target of the action.

Specifically, since the aforementioned polyethylene-glycolated AS1051 has an activity of inhibiting platelet aggregation similar to that of CHH-B and AS1051 and it does not show antigenicity upon its administration to animals, it can be utilized as an antithrombotic drug.

In a pharmaceutical composition, the peptide of the present invention may be used as it is or as a pharmaceutically acceptable salt thereof. The peptides can be used each alone or as a mixture of two or more kinds of them. Other active ingredients may also be added. Further, it may be mixed with other materials for use in conventional pharmaceutical preparations, for example, ingredients including proteins such as serum albumin, buffering agents, salts for osmotic adjustment, carriers and excipients.

Examples of the dosage form include tablet, capsule, subtilized granule, syrup, suppository, ointment, injection, eye drop and so forth. Among these, injection is preferred. As the administration method, any of intravenous administration, subcutaneous administration, intramuscular administration, oral administration, instillation, enteral administration and so forth may be used, but intravenous administration, subcutaneous administration, intramuscular administration and so forth are preferred among them.

As for dose for an animal or human, a dose of polyethylene-glycolated AS1051, for example, in the range from 0.1 μg/kg to 100 mg/kg as the amount of the peptide can usually be expected to provide the desired effect, and a dose that can provide the optimal drug efficacy can be selected in this range.

EXAMPLES

Hereafter, the present invention will be more specifically explained with reference to the following examples.

Example 1

Cloning of CHH-B α-Chain Protein Gene

Cloning of a CHH-B α-chain protein gene was performed according to the method of N. Fukuchi et al. (WO95/08573). Specifically, it was performed by the following procedure.

<1> Preparation of cDNA Library of Crotalus horridus horridus (1) Extraction of mRNA from Crotalus horridus horridus A poison gland of Crotalus horridus horridus was extracted, immediately frozen with liquid nitrogen and stored until use. 1.7 g of the poison gland was disrupted in 20 ml of an RNA extraction solution (4 M guanidium isothiocyanate hydrochloride, 0.1 M Tris-HCl (pH 7.5), 1% β-mercaptoethanol, 0.1% lauryl sarcosyl sodium salt) by using a Polytron homogenizer (Kinematica). This disruption solution was centrifuged at 10,000×G for 10 minutes to remove insoluble matters. The supernatant was overlaid on an equal volume of a density equilibrated buffer (4 M cesium chloride, 10 mM disodium ethylenediaminetetraacetate, pH 7.5) in an ultracentrifugation tube and centrifuged at 30,000 rpm at 20° C. for 18 hours to separate 600 μg of total RNA.

mRNA was prepared from total RNA by using a POLY(A) Quik mRNA Extraction Kit (Stratagene) according to the protocol attached to the kit. That is, 500 μg of the obtained total RNA was adsorbed on an oligo dT column and the column was washed twice with 200 μl of a high salt concentration buffer and three times with 200 μl of a low salt concentration buffer. Then, 200 μl of elution buffer was passed through the column at 65° C. four times to separate and purify mRNA (10 μg).

(2) Synthesis of cDNA cDNA was synthesized by using a Time Savor DNA synthesis kit (Pharmacia) according to the protocol attached to the kit. That is, 3 μg of the purified mRNA was mixed with a first strand reaction mixture containing 0.3 μg of random hexamer primers, 1 mM dithiothreitol and reverse transcriptase and the mixture was allowed to react at 37° C. for 1 hour to synthesize a first strand.

This reaction mixture was mixed with a second strand reaction mixture containing Escherichia Coli RNase H and Escherichia coli DNA polymerase and the mixture was allowed to react at 12° C. for 30 minutes and at 22° C. for 1 hour to synthesize cDNA. Further, the reaction mixture was incubated at 65° C. for 10 minutes and then treated with phenol/chloroform to inactivate the enzyme. Subsequently, the reaction mixture was centrifuged at 400×G for 2 minutes by using a gel filtration spin column attached to the kit to remove unreacted primers and obtain double-stranded cDNA (3 μg).

(3) Preparation of cDNA Library

An EcoRI/NotI adaptor attached to the Time Savor DNA kit was ligated to both ends of the double-stranded cDNA obtained above, according to the protocol attached to the kit. That is, 3 μg of the cDNA, 3 μl of the EcoRI/NotI adaptor, 30 μl of a polyethylene glycol buffer, 1 μl of an ATP solution and 1 μl of T4 DNA ligase were mixed and subjected to a ligation reaction at 16° C. for 1 hour. The reaction mixture was further incubated at 65° C. for 10 minutes to inactivate an enzymatic activity. Then, 1.5 µl of ATP solution and 1 µl of T4 polynucleotide kinase were added and the mixture was allowed to react at 37° C. for 30 minutes, phosphorylating the 5' end of the adaptor. Then, the reaction mixture was further incubated at 65° C. for 10 minutes and subjected to a phenol/chloroform treatment so that the enzymatic activity was inactivated. Subsequently, the reaction mixture was centrifuged at 400×G for 2 minutes by using a gel filtration spin column attached to the kit, to remove the unreacted adaptor.

The cDNA ligated with the adaptor at its both ends was ligated to the EcoRI site of the lambda phage vector λZAPII (Stratagene) to prepare recombinant phage DNA. That is, to 400 ng of the cDNA ligated with the adaptor, 1 µg of λZAPII/EcoRI/CIAP arm, a ligation buffer (100 mM Tris-HCl (pH 7.6), 25 mM magnesium chloride, 300 mM sodium chloride) were added, and an equivalent volume of an enzyme solution containing T4 DNA ligase, Solution B (Ligation Kit manufactured by Takara Shuzo) was added and the mixture was subjected to a ligation reaction at 26° C. for 10 minutes.

The recombinant phage DNA obtained as described above was packaged by using a packaging kit GIGAPACKII GOLD (Stratagene) according to the protocol attached to the kit. That is, 3 µg of the λZAPII arm DNA ligated with the cDNA and a packaging extraction solution of the kit were mixed and allowed to react at 22° C. for 2 hours to perform packaging. To this reaction mixture, 500 µl of a phage dilution solution (0.58% sodium chloride, 0.2% magnesium sulfate, 50 mM Tris-HCl (pH 7.5), 0.01% gelatin) was added.

The titer of the obtained recombinant phage was checked and then a phage library was prepared by using a half volume of the phage packaging reaction mixture and *Escherichia coli, E. coli* XL-1 Blue (Stratagene), as recipient bacteria. That is, phages diluted with the phage dilution solution and recipient bacteria were plated on 10 of plaque-forming medium plates (1% Bacto trypton, 0.5% yeast extract, 0.5% sodium chloride, 1 mM magnesium sulfate, 0.2% maltose) having a diameter of 150 mm at such a density that 20,000 plaques per plate should be obtained, and cultured at 37° C. for 12 hours to obtain a recombinant phage library.

<2> Acquisition of Probe DNA for Isolation of Target Gene (1) Amplification of Partial Fragment of Target Gene by RT-PCR Method A DNA fragment coding for the peptide inhibiting binding of the von Willebrand factor to platelets was amplified by the RT-PCR method using total RNA extracted from *Crotalus horridus horridus* as a raw material.

A site not having many degenerated codons was selected based on the amino acid sequence of the peptide, shown in SEQ ID NO: 1 (N. Fukuchi et al., supra) to prepare primers for reverse transcription polymerase chain reaction (RT-PCR). Chemical synthesis of the primers was trusted to Biologica. The nucleotide sequences of these primers are shown in SEQ ID NOS: 2 and 3 in Sequence Listing. It is noted that the 3rd and 6th nucleotides are each a mixture of A and G and the 12th nucleotide is a mixture of T, C, A and G in SEQ ID NO: 2. In SEQ ID NO: 3, the 3rd nucleotide is a mixture of T, C, A and G, the 6th and 15th nucleotides are each a mixture of T and C, and the 9th nucleotide is a mixture of A and G.

Total RNA of *Crotalus horridus horridus* prepared as described above was subjected to RT-PCR by using the above primers. The first strand was synthesized by mixing 5 µl of the total RNA with 2.5 µl of reverse transcriptase SUPERSCRIPT II (GIBCO), 20 µl of a first strand buffer attached to the enzyme solution, 10 µl of 0.1 M dithiothreitol and 5 µl of 10 mM dNTP and allowing the mixture to react at 42° C. for 1 hour. The reaction mixture was incubated at 95° C. for 5 minutes to inactivate the reverse transcriptase. Subsequently, PCR was performed by using the first strand as a template. That is, 5 µl of the first strand reaction mixture, 10 µl of a PCR buffer, 5 µl of 10 mM dNTP, 800 pmol each of primers and 10 units of Taq polymerase were mixed. Then, a reaction was performed by using a DNA thermal cycler (Perkin-Elmer) with a cycle of reactions at 95° C. for 0.5 minutes, at 52° C. for 1 minute and at 72° C. for 2 minutes, which was repeated 25 times.

This PCR reaction mixture was subjected to 2% agarose gel electrophoresis to analyze the amplified DNA. As a result, a DNA band was observed at position of about 300 base pairs.

(2) Determination of Nucleotide Sequence of Amplified Fragment

The DNA fragment amplified as described above was subcloned in a plasmid by using a pCR-ScriptSK(+) cloning kit (Stratagene) according to the protocol attached to the kit. That is, the PCR reaction mixture was mixed with a ligation buffer, 1 mM ATP, 10 ng of pCRscript (Stratagene) as a vector, 5 units of restriction enzyme SrfI and T4 DNA ligase and a ligation reaction was performed at 25° C. for 1 hour. Then, the reaction mixture was incubated at 65° C. for 10 minutes to inactivate the ligase. *E. coli* DH5α was transformed by the competent cell method using the reaction product, plated on an L-Ap plate (1% Bacto trypton, 0.5% yeast extract, 0.5% sodium chloride, 100 µg/ml of sodium ampicillin) and cultured at 37° C. for 18 hours. Microbial cells forming colonies were separated from the plate and a part of them were cultured in a liquid medium and a plasmid was prepared by the alkaline method (Molecular Cloning, 2nd edition, Vol. 1, Cold Spring Harbor Press). This plasmid was designated as pCHAprobe.

The nucleotide sequence of a cloned fragment of pCHAprobe was analyzed by the dye terminator method using a DNA sequencer A373 (Applied Biosystems) and M13M4 or M13reverse (Takara Shuzo) as a primer according to the instructions attached to the sequencer. As a result, it was found that the cloned DNA fragment was composed of 272 base pairs and had the nucleotide sequence shown in SEQ ID NO: 4. When this sequence was translated into an amino acid sequence, the sequence corresponded to a part of the target peptide and thus it was proved that the obtained cloned fragment was a part of the gene coding for the target peptide, CHH-B α-chain protein subunit (AS1051).

(3) Labeling of Probe pCHAprobe was digested with restriction enzymes SacI and BamHI for which restriction sites were present at both ends of the cloned insert fragment, and a DNA fragment having a size of 340 base pairs was separated by 2% agarose gel electrophoresis. DNA was recovered by using a DNA recovery kit (Takara EASYTRAP: Takara Shuzo) according to the protocol attached to the kit. 25 ng of the DNA was labeled with a radioisotope by using [α-$^{32}$P]dCTP and a random primer labeling kit (Takara Shuzo). Unreacted [α-$^{32}$P]dCTP was removed from the labeling reaction mixture by using a gel filtration Nick column (Pharmacia) to obtain a labeled probe.

<3> Acquisition of Target Gene by Plaque Hybridization

The cDNA phage library was screened for a gene coding for the total length of the AS1051 peptide by plaque hybridization using the above probe.

The plaques were transferred from the plate, in which plaques of the λZAPII cDNA phage library were formed as described above, to a nylon filter Hybond-N (Amersham) according to the instructions attached to the filter. This filter was subjected to an alkaline treatment to lyse the phages and baked at 80° C. for 2 hours so that the phage DNA was immobilized on the filter.

This filter was hybridized with 1×10$^6$ cpm/ml of $^{32}$P-labeled probe in a solution containing 5×SSPE buffer (20× SSPC: 3.6 M sodium chloride, 0.2 M sodium phosphate buffer (pH 7.7), 20 mM disodium EDTA), 30% formamide, 5× Denhart's solution (100× Denhart's solution: 2% bovine serum albumin, 2% Ficoll 400, 2% polyvinylpyrrolidone) and 0.5% SDS at 37° C. for 16 hours. Then, the filter was washed twice in 6×SSC (20×SSC: 3 M sodium chloride, 0.3 M trisodium citrate) and 0.1% SDS at room temperature and further washed twice in 2×SSC and 0.1% SDS at 50° C. to remove probes non-specifically bound to the filter. This filter was exposed to X-ray film HP20 (Fuji Photo Film) at –80° C. for 24 hours. Clones located at positions corresponding to positive spots of the film were isolated from the phage plate as positive clones in the primary screening. Similar screening operation was repeated to obtain positive clones each forming a single plaque.

The λZAPII cDNA phages of the obtained positive clones were infected with a helper phage ExAssist (Stratagene) and then were allowed to infect SOLR cells (Stratagene), which are non-amber suppressor *Escherichia coli*, to obtain *Escherichia coli* harboring a plasmid wherein a cDNA fragment was inserted into the EcoRI site of a plasmid pBluescriptSK(–) (Stratagene). Plasmids were prepared from the microbial cells by the alkaline SDS method and the nucleotide sequences of the insert fragments were determined by using a DNA sequencer A373 (Applied Biosystems).

As a result, four positive clones had nucleotide sequences coding for the target peptide and plasmids having these were designated as pCHA1, pCHA2, pCHA3 and pCHA4, respectively. The *E. coli* HB101/pCHA1 (*E. coli* AJ13023) strain harboring pCHA1 was deposited at National Institute of Bioscience and Human-Technology, Agency of Industrial Science and Technology, Ministry of International Trade and Industry (postal code: 305-8566, 1-3, Higashi 1-chome, Tsukuba-shi, Ibaraki-ken, Japan) as an international deposition under the provisions of the Budapest Treaty on Aug. 12, 1994, and received an accession number of FERM BP-4781. The nucleotide sequence of the gene coding for the AS1051 peptide cloned as described above is shown as SEQ ID NO: 5 and the amino acid sequence of the peptide encoded by this gene is shown as SEQ ID NO: 6 in Sequence Listing. This gene has a typical secretion signal composed of 23 amino acids starting with methionine which is a translation initiation amino acid.

Example 2

Construction of Expression System for CHH-B α-Chain Protein (AS1051) by Using *Escherichia coli*

<1> Construction of Expression System for Wild-Type CHH-B α-Chain Protein

An expression system for the mutation-unintroduced CHH-B α-chain protein (AS1051-WT) by using *Escherichia coli* was constructed by using the gene obtained in Example 1 as follows. A vector for expression in *Escherichia coli* was constructed by using the cloned gene.

To incorporate the gene coding for the AS1051 peptide (except for a signal peptide) into an expression vector, DNA primers were synthesized for amplification by PCR. At that time, as the 5' end primer, a primer including a NcoI recognition sequence (ASBN: SEQ ID NO: 7) was used so that the 5' end of the amplified fragment should have the NcoI site. Also, this primer had a nucleotide sequence ATG (nucleotide numbers 10 to 12 in SEQ ID NO: 7), which was a translation initiation codon, before a codon of the N-terminal amino acid of the AS1051 peptide, i.e., aspartic acid, on the 5' end side. This initiation codon overlapped the NcoI recognition sequence (nucleotide numbers 8 to 13 in SEQ ID NO: 7). As the 3' end primer, a primer including a HindIII recognition sequence (SEQ ID NO: 8, HindIII recognition sequence corresponds to nucleotide numbers 4 to 9) was used.

The gene coding for the AS1051 peptide was amplified by PCR using these primers. PCR was performed with a cycle of reactions at 94° C. for 15 seconds, at 35° C. for 1 minute and at 72° C. for 2 minutes, which was repeated 25 times. The PCR reaction mixture was subjected to a phenol/chloroform treatment to inactivate Taq polymerase. The amplified DNA fragment of 400 base pairs was purified by ethanol precipitation and digested with restriction enzymes BamHI and HindIII. This DNA fragment and a plasmid pUC18 (Takara Shuzo) digested with restriction enzymes BamHI and HindIII were ligated by using a Ligation Kit (Takara Shuzo). The *E. coli* JM109 strain was transformed by the competent cell method with the obtained plasmid and cultured on an ampicillin-containing plate at 37° C. for 16 hours to obtain a transformant.

A plasmid was prepared from a grown transformant by the alkaline SDS method. Construction of the target plasmid was confirmed by determining the nucleotide sequence by using the M13M4 and M13RV primers (the both are produced by Takara Shuzo) and a 377PRISM DNA sequencer (Perkin-Elmer). The prepared plasmid was designated as pUCASBNH. The pUCASBNH was digested with restriction enzymes NcoI and HindIII and subjected to agarose gel electrophoresis to separate and purify DNA of 400 base pairs. This DNA was ligated with a product obtained by digesting an expression vector pTrcHisA (Invitrogen) with restriction enzymes NcoI and HindIII, by using the Ligation Kit. The *E. coli* JM109 strain was transformed with the obtained plasmid by the competent cell method and cultured on an ampicillin-containing plate at 37° C. for 16 hours to obtain a transformant. The expression vector obtained as described above was designated as pTrcASWT. The above plasmid construction process is shown in FIG. 1.

<2> Construction of Expression System for Mutant CHH-B α-Chain Protein

An expression system using *Escherichia coli* for the protein wherein the cysteine residue in position 81 was mutated to an alanine residue (AS1051-Ala) was constructed as follows. A mutation was introduced into the AS1051 gene by the site-directed nucleotide sequence mutation method described in PCR protocols (Academic Press edition) so that a cysteine residue (cysteine residue in position 81 in SEQ ID NO: 1) not involved in a disulfide bond in the AS1051 peptide was replaced with alanine. PCR was performed by using pCHA1 as a template and the primer ASBN (SEQ ID NO: 7) and a newly synthesized primer ASAlaR (SEQ ID NO: 9), or the primer ASH (SEQ ID NO: 8) and a newly synthesized ASAlaF (SEQ ID NO: 10). Each reaction product was subjected to agarose gel electrophoresis and an amplified DNA fragment was extracted from the gel. The second PCR was performed by using each DNA fragment as a template and the primers ASBN and ASH to prepare a mutant gene.

The PCR-amplified DNA was digested with a restriction enzyme and subjected to agarose gel electrophoresis, and DNA of 400 base pairs was extracted from gel. This DNA was digested with restriction enzymes BamHI and HindIII. This DNA fragment was ligated with a plasmid pUC18 (Takara Shuzo) digested with restriction enzymes BamHI and HindIII, by using a Ligation Kit (Takara Shuzo). The *E. coli* JM109 strain was transformed with the obtained plasmid by the competent cell method and cultured on an ampicillin-containing plate at 37° C. for 16 hours to obtain a transformant.

Figure 2:
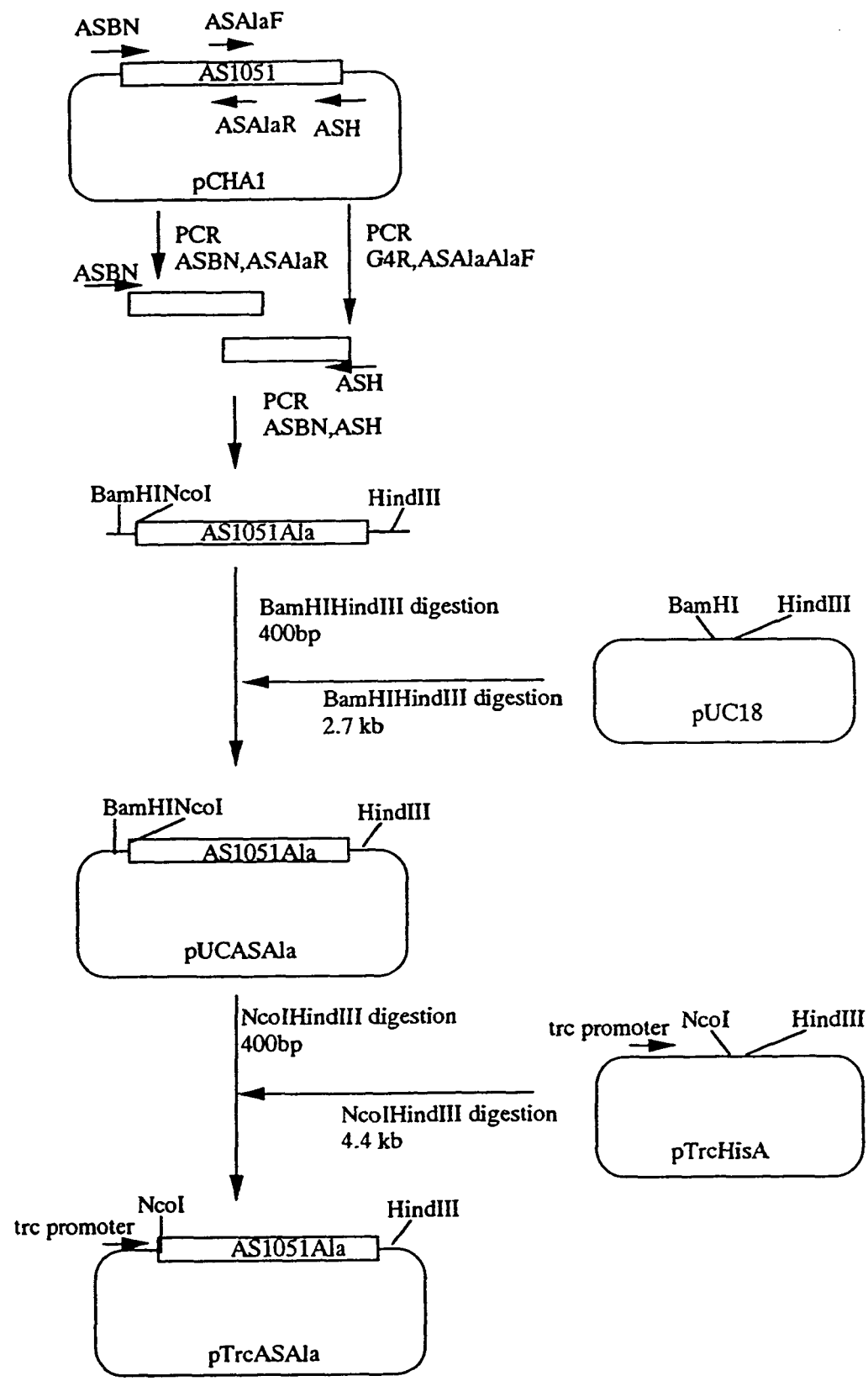
FIG. 2 shows a construction process of vector pTrcASAla which expresses variant-type AS1051 (AS1051-Ala) in which a cysteine residue is replaced with an alanine residue.

A plasmid was prepared from a grown transformant by the alkaline SDS method. Construction of the target plasmid was confirmed by determining the nucleotide sequence by using the M13M4 and M13RV primers (both from Takara Shuzo) and a 377PRISM DNA sequencer (Perkin-Elmer). The prepared plasmid was designated as pUCASAla. The plasmid pUCASAla was digested with restriction enzymes NcoI and HindIII and subjected to agarose gel electrophoresis to separate and purify DNA of 400 base pairs. This DNA fragment was ligated with a product obtained by digesting an expression vector pTrcHisA (Invitrogen) with restriction enzymes NcoI and HindIII, by using the Ligation Kit. The *E. coli* JM109 strain was transformed with the obtained plasmid by the competent cell method and cultured on an ampicillin-containing plate at 37° C. for 16 hours to obtain a transformant. The expression vector prepared as described above was designated as pTrcASAla. The above plasmid construction process is shown in FIG. 2.

Example 3

Production of AS1051-WT and AS1051-Ala by *E. coli* and Preparation of Active Form by Refolding of AS1051-WT and AS1051-Ala <1> Preparation of Inclusion Body of AS1051-WT and AS1051-Ala The transformant *E. coli* JM109 strains harboring the expression vectors pTrcASWT and pTrcASAla for AS1051-WT and AS1051-Ala, respectively, were each cultured at 37° C. in L-broth (1% Bacto trypton, 0.5% yeast extract, 0.5% sodium chloride, 100 μg/ml sodium ampicillin) by using Sakaguchi flasks. IPTG (isopropyl-β-thiogalactopyranoside) was added at 10 mM when the turbidity reached 0.5 and they were further cultured at 37° C. for 4 hours. The microbial cells were collected by centrifugation and washed. Then, the microbial cells were suspended in a 0.5 M EDTA solution. Then, lysozyme was added thereto and the suspension was left at room temperature for 1 hour. The suspension of the microbial cells was disrupted by an ultrasonicator (200 W, 5 minutes) and the disrupted mixture was centrifuged to obtain inclusion bodies as precipitates.

<2> Preparation of Active Form by Refolding of AS1051-WT and AS1051-Ala

Figure 3A:
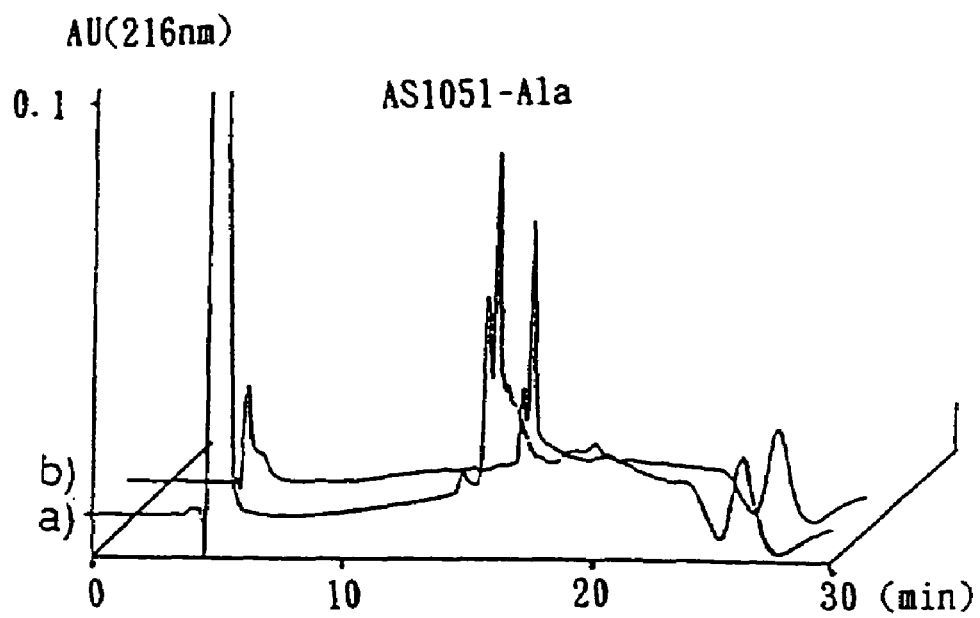
FIG. 3 shows results of analysis by reverse phase HPLC, of refolded AS 1051-WT (FIG. 3a) and AS1051-Ala (FIG. 3b) samples before dialysis (a) and after dialysis (b). Time is represented on the horizontal axis and absorbance (216 nm), i.e., the amount of dissolved proteins is represented on the vertical axis.
Figure 3B:
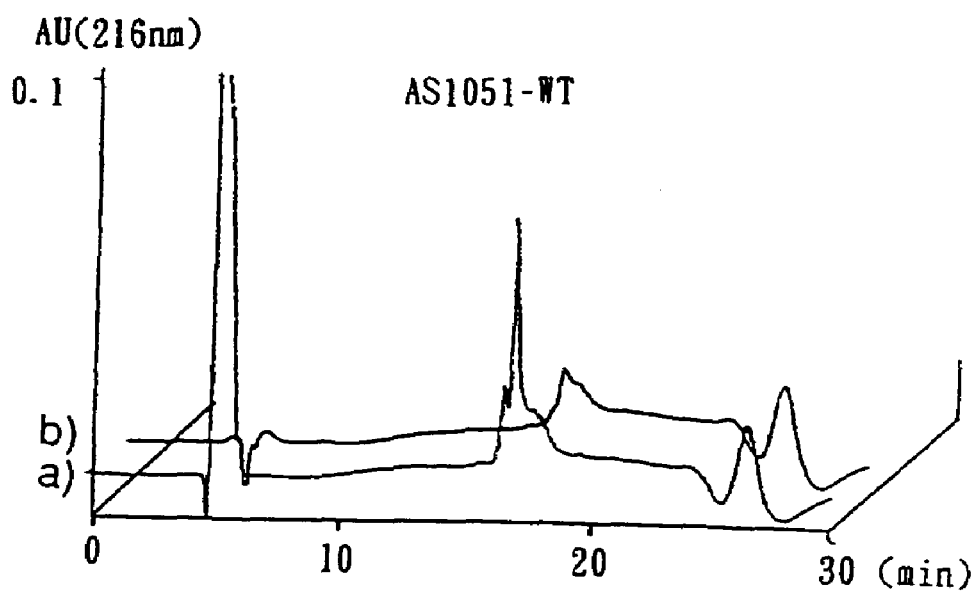

The obtained inclusion bodies were dissolved in 0.5 M Tris-HCl buffer (pH 8.5) containing 7 M guanidine hydrochloride and 10 mM EDTA. Then, distilled water was added in a volume of 2.5 times the solution and the mixture was left overnight at 4° C. The solution was dialyzed against 0.9% saline by using a dialysis membrane utilizing Spectra Por1 (Spectra) to remove guanidine hydrochloride. FIG. 3 shows the results of fractionation of solutions of AS1051-WT and AS1051-Ala before and after the dialysis, by high performance liquid chromatography (HPLC) using a reverse phase column (Pegasil ODS300, Senshu Kagaku). In FIG. 3, a) represents the results for the solution before dialysis and b) represents the results for the solution after dialysis. It was found that AS1051-Ala was stable even when guanidine hydrochloride was removed, whereas the AS1051-WT protein obtained by refolding was insolubilized after removal of guanidine hydrochloride by dialysis.

To the solution of AS1051-Ala after the dialysis, ⅙ volume of 0.5 M ammonium acetate buffer (pH 4.5) was added and the mixture was adsorbed on an ion exchange column using CM-TOYOPEARL 650S (2.6×40 cm) and eluted with Elution solution A (50 mM ammonium acetate buffer (pH 4.5)) and Elution solution B (0.5 M ammonium acetate buffer (pH 6.4)). The elution was performed with a solution of A:B=75:25 for 20 minutes, and then with a linear gradient of from A:B=75:25 to A:B=50:50 for 30 minutes. Thus, an eluted fraction containing purified AS1051-Ala was obtained.

Example 4

Antigenicity Test of AS1051-Ala in Guinea Pig

To confirm the antigenicity of the AS1051 protein in which the cysteine residue at position 81 was replaced with the alanine residue (AS1051-Ala), in a guinea pig, a test was performed as follows. The proteins were quantified by a microassay method using a Bio-Rad Protein Assay (Bio-Rad) by using bovine serum albumin (BSA) as a standard.

Figure 4:
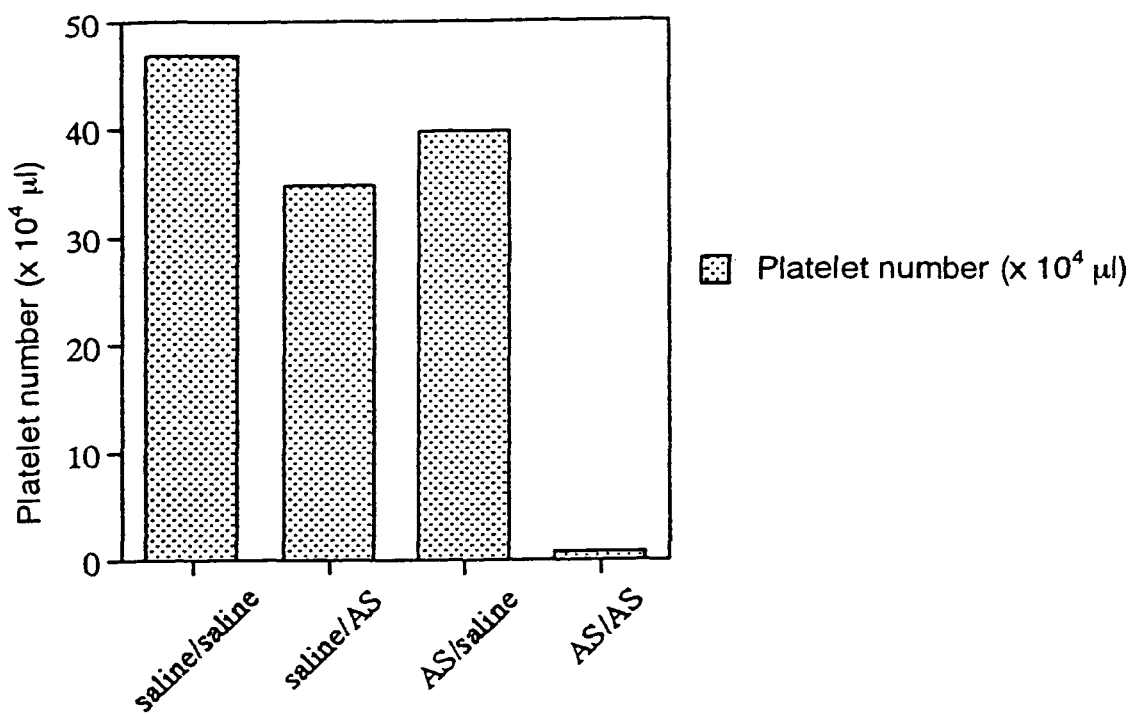
FIG. 4 shows the number of platelets in guinea pigs after repetitive administrations of AS1051-Ala.

To female Hartley guinea pigs (body weight 200 to 250 g), AS1051-Ala (300 μg/kg) or a physiological saline solution was administered from auricular veins three times every other day. The dose was 1 ml/kg and each group was composed of 10 animals (n=10). Following 3 weeks after the third administration, each administration group was further divided into two groups, and AS1051-Ala (300 μg/kg) (n=5 each) or a physiological saline (n=5 each) was administered to each group. About 20 minutes later, abdominal section was performed under etherization and 8 ml of blood was collected from the abdominal aorta (0.38% sodium citrate was added) by using a 23 G injection needle. The number of platelets in the collected blood was measured by using an automatic cell counter (Sysmex E-2000, To a Medical Electronics). The results are shown in FIG. 4. A marked decrease of platelets was observed only in the group in which AS1051-Ala was administered at preliminary and final administrations (AS/AS group). In the group in which the physiological saline solution was administered at preliminary administration and AS1051-Ala was administered at final administration (saline/AS group), the number of platelets was the same as that of the control group (the saline solution at both of preliminary and final administrations (saline/saline group)). Therefore, it was considered that the decrease of platelets observed in the AS/AS group was attributable to the antigenicity of AS1051-Ala administered at preliminary administration.

Figure 5:
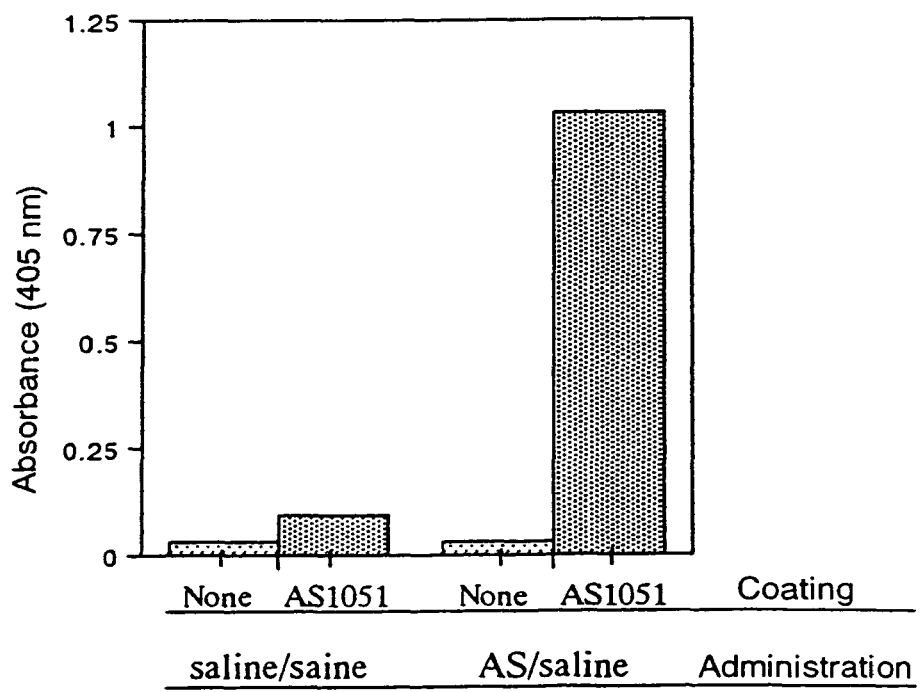
FIG. 5 shows results of detection of anti-AS1051-Ala antibodies in plasma of guinea pigs after repetitive administrations of AS1051-Ala.

Further, plasma was separated from the collected blood by centrifugation (4° C., 2700 rpm, 10 minutes), and the presence of antibodies to AS1051-Ala was determined by an enzyme-linked immunosorbent assay (ELISA) method. 50 μl of AS1051-Ala (1 μl/ml) or only a buffer was added to each well of a 96-well plate for ELISA and left overnight at 4° C. to coat the well. Then, each well was washed three times with PBS (phosphate-buffered saline) containing 0.05% Tween-20 and blocked with PBS (150 μl) dissolving 5% skim milk. Each well was further washed three times. 50 μl of the collected guinea pig plasma was added thereto and it was left at 37° C. for 1 hour. Then, each well was washed three times. 50 μl of a solution obtained by diluting alkaline phosphatase-labeled rabbit anti-guinea pig IgG (H+L) antibodies (Zymed) 500-fold with a dilution buffer (0.05 M Tris-HCl (pH 8.1), 1 mM $MgCl_2$, 0.15 M NaCl, 0.05% Tween-20, 0.02% $NaN_3$, 1% bovine serum albumin) was added and it was left at 37° C. for 1 hour. Each well was washed three times, and 1 mg/ml of a chromogenic substrate (p-nitrophenylphosphate) solution (1 M diethanolamine (pH 9.8)/0.5 mM $MgCl_2$) was added. After an appropriate time for the reaction, absorption was measured at 405 nm. FIG. 5 shows absorption of reaction mixtures in the wells coated with AS1051-Ala (AS1051) and the wells without coating (None) for the AS/saline group and the saline/saline group. As a result of the measurement, the presence of antibodies bound to AS1051-Ala was demonstrated in the AS/saline group.

Example 5

Preparation of Polyethylene-Glycolated AS1051 Protein (AS1051-PEG)

(1) Method Using PEG-Ating Reagent Having Molecular Weight of 5000

The polyethylene-glycolated protein of the present invention (AS1051-PEG) was prepared as follows. In the same manner as in Example 3, inclusion bodies of AS1051-WT prepared by using *E. coli* were dissolved in 0.5 M Tris-HCl buffer (pH 8.5) containing 7 M guanidine hydrochloride and 10 mM EDTA. Then, distilled water was added in a volume 2.5 times the solution and the mixture was left overnight at 4° C.

Further, to this solution, a polyethylene-glycolating reagent having a molecular weight of about 5000 (Methoxy-PEG-mal, MW 5000, Item No.: M-MAL-5000, Shearwater Polymers), which had maleimide groups, was added at a concentration of 0.2 mg/ml, and the mixture was left at room temperature for 3 hours. This solution was dialyzed against distilled water by using a dialysis membrane utilizing Spectra Por1 (Spectra) to remove guanidine hydrochloride. To the solution after the dialysis, ⅛ volume of 0.5 M ammonium acetate buffer (pH 4.5) was added, and the solution was adsorbed on an ion exchange column using CM-TOYOPEARL 650S (2.6×40 cm) and eluted by using Elution solution A (50 mM ammonium acetate buffer (pH 4.5)) and Elution solution B (0.5 M ammonium acetate buffer (pH 6.4)). The elution was performed with a linear gradient of from A:B=80:20 to A:B=70:30 (20 minutes), and then with a linear gradient of from A:B=70:30 to A:B=55:45 (30 minutes). Thus, an eluted fraction containing purified AS1051-PEG was obtained.

(2) Method Utilizing PEG-Ating Reagent Having Molecular Weight of 20,000

The polyethylene-glycolated AS1051 protein of the present invention (AS1051-PEG20000) was prepared by using a polyethylene-glycolating reagent having a molecular weight of 20,000 (Methoxy-PEG-mal, MW 20,000, Item No.: M-MAL-20000, Shearwater Polymers) as follows. In the same manner as in Example 3, inclusion bodies of AS1051-WT prepared by using *E. coli* were dissolved in 0.5 M Tris-HCl buffer (pH 8.5) containing 7 M guanidine hydrochloride and 10 mM EDTA. Then, distilled water was added in a volume 2.5 times the solution, and the mixture was left overnight at 4° C.

Further, to this solution, the polyethylene-glycolating agent having a molecular weight of 20,000, which had maleimide groups, was added at a concentration of 0.8 mg/ml, and the mixture was left at room temperature for 3 hours. This solution was dialyzed against a physiological saline solution by using a dialysis membrane utilizing Spectra Por1 (Spectra) to remove guanidine hydrochloride, adsorbed on an ion exchange column using TSK-gel CM-5PW (0.75×7.5 cm) and eluted with Elution solution A (50 mM ammonium acetate buffer (pH 4.5)) and Elution solution B (0.5 M ammonium acetate buffer (pH 6.4)). The elution was performed with a linear gradient of from A:B=100:0 to A:B=40:60 (20 minutes) and then with a linear gradient of from A:B=40:60 to A:B=0:100 (5 minutes). Thus, an eluted fraction containing purified AS1051-PEG20000 was obtained.

Example 6

Structure of AS1051-PEG

SDS electrophoresis revealed that the molecular weight of the obtained AS1051-PEG was 25 kDa, about 10 kDa larger than that of the AS1051-Ala that was not polyethyleneglycolated (15 kDa). Since polyethylene glycol is observed in a size twice as large as the original molecular weight due to hydration in SDS electrophoresis, it was confirmed that one molecule of polyethylene glycol (molecular weight of about 5000) was bound in one molecule of AS1051-PEG. Further, the molecular weight of the AS1051-PEG20000 was 55 kDa, which was about 40 kDa larger than that of AS1051-Ala. As in the case of AS1051-PEG, it was confirmed that one molecule of polyethylene glycol (molecular weight of about 20,000) was bound in one molecule of AS1051-PEG20000.

Subsequently, the polyethylene glycol-binding position in AS1051-PEG and linkage of disulfide bonds of the other cysteine residues were determined as follows. AS1051-PEG (100 μg) was digested with lysyl endopeptidase (5 μg, Wako Pure Chemical Industries) in 0.1 M Tris-HCl buffer (pH 8.5) containing 2 mM EDTA at 37° C. for 5 hours and fractionated by high performance liquid chromatography using a reverse phase column (Vydac 218TP54, Vydac). Elution was performed with a linear gradient of water/acetonitrile containing 0.1% trifluoroacetic acid (TFA) (acetonitrile concentration of from 0 to 50% for 10 minutes, acetonitrile concentration of from 50% to 100% for 5 minutes). Thus, peptide chains digested with lysyl endopeptidase were obtained as Peaks 1 to 6 (FIG. 6).

The amino acid sequence of each peptide chain was analyzed by using a protein sequencer Model 476A (Applied Biosystems). Since two cysteine residues were contained in the chain of Peak 3, it was concluded that these two cysteine residues were coupled to form a disulfide bond. Further, it was found that Peak 5 was composed of total three peptide chains, wherein two peptide chains containing one cysteine residue and one peptide chain containing two cysteine residues were coupled through disulfide bonds. The peptide chains of this Peak 5 were further digested with V8 protease (5 μg, Wako Pure Chemical Industries) in 10 mM ammonium carbonate buffer at 25° C. for 24 hours and fractionated by high performance liquid chromatography using a reverse phase column (Pegasil ODS-II, Senshu Kagaku). Elution was performed with a linear gradient of water/acetonitrile containing 0.1% (TFA) (acetonitrile concentration of from 0 to 50% for 20 minutes). Thus, peptide chains digested with V8 protease were separately collected and their amino acid sequences were analyzed.

As a result, it was found that the polyethylene glycol chain was bonded to a cysteine residue corresponding to amino acid number 81 in SEQ ID NO: 1 and that the peptides of Peak 5 had such a disulfide bond as shown in FIG. 6. The scheme of disulfide bonds in AS1051-PEG determined as described above was the same as in the reported AS1051 (N. Fukuchi et al., WO 95/08573) or other similar proteins originating from snake venom.

Example 7

In Vitro Activity of AS1051-PEG

<1> Measurement of Platelet Aggregation Inhibitory Activity of AS1051-PEG

Figure 7A:
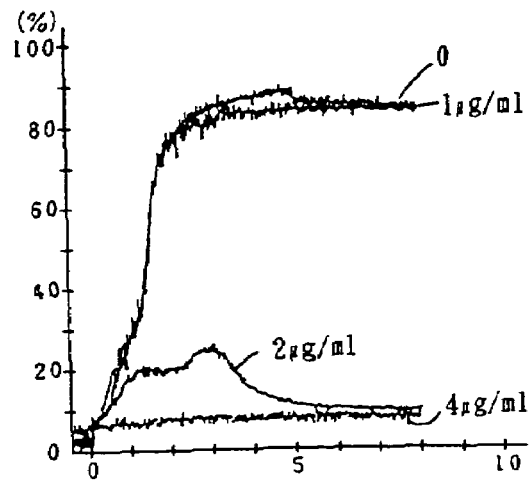
FIG. 7 shows inhibitory activities of AS1051-Ala (FIG. 7a) and AS1051-PEG (FIG. 7b and FIG. 7c) on ristocetin aggregation.
Figure 7B:
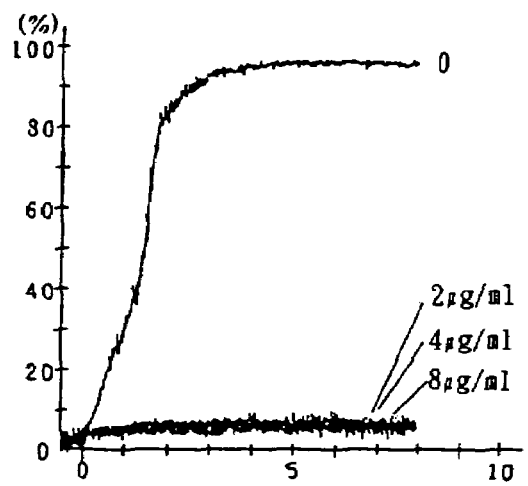
Figure 7C:
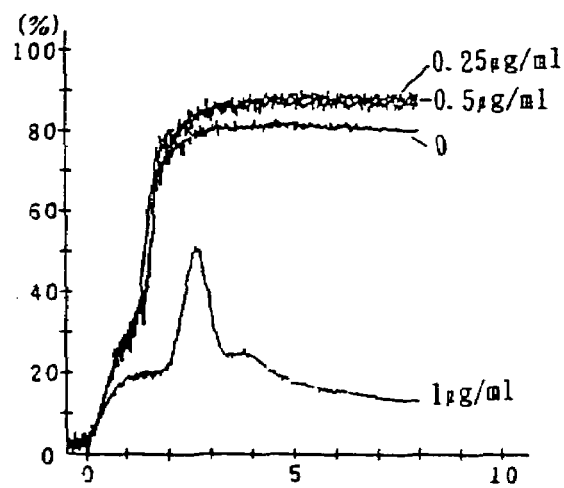

The platelet aggregation inhibitory activity of AS1051-PEG obtained in Example 5 was measured by a method described below. First, to human blood collected from a vein, 0.38% sodium citrate was added and the mixture was centrifuged at 1000 rpm for 15 minutes to obtain platelet-rich plasma. The platelet aggregation inhibitory activities of AS1051-PEG and AS1051-Ala were measured by an aggregometer (HEMA TRACER 801, Niko Bioscience). A test sample was added to 100 µl of platelet-rich plasma in advance, stirred at 37° C. for 2 minutes and incubated. Then, $\frac{1}{10}$ volume of an aggregation-inducing substance at a 10-fold concentration was added and platelet aggregation was observed for 8 minutes. As the aggregation-inducing substance, ristocetin (1.2 mg/ml, Sigma), collagen (10 µg/ml, MC Medical) and adenosine diphosphate (10 µM, MC Medical) were used. As shown in FIG. 7, the ristocetin aggregation inhibitory activity of AS1051-PEG was slightly stronger than that of AS1051-Ala. Further, neither AS1051-Ala nor AS1051-PEG inhibited aggregation by collagen or aggregation by adenosine diphosphate.

<2> Measurement of Activity of Inhibiting Binding of von Willebrand Factor (vWF) to Platelets Inhibition of binding of platelets and von Willebrand factor (vWF) by AS1051-Ala and AS1051-PEG was determined by using immobilized platelets and $^{125}$I labeled vWF.

$^{125}$I-labeled vWF was prepared by a method described below. In a tube for $^{125}$I labeling, 1.5 ml of Iodogen solution (0.5 mg/ml, Piearce) in dichloromethane was added in advance and the solvent was removed under a nitrogen flow to immobilize Iodogen as a solid phase. High molecular weight vWF (0.19 mg/1.5 ml) obtained by gel filtration was added to the Iodogen-immobilized tube. Then, 18.5 Mbq of Na$^{125}$I was added and the mixture was allowed to react at room temperature for 2 minutes. Then, the reaction mixture was applied to a PD10 column (Pharmacia Biotech), which was blocked with bovine serum albumin (BSA) and washed in advance, and eluted with TBS (20 mM Tris-HCl (pH 7.4), 0.15 M NaCl). The eluate was collected as 0.5 ml fractions and the $^{125}$I specific activity of each fraction was determined by using a gamma counter, Packard Multi Prias 4. Fractions containing a large amount of $^{125}$I-vWF were collected, divided into several tubes and stored at −80° C. until use.

Botrocetin was purified as follows. 1 g of a lyophilized crude venom preparation of *Botrops jararaca* (Sigma, V-5625) was dissolved in 20 ml of 0.9% saline. Insoluble substances were removed by centrifugation and the supernatant was subjected to gel filtration using a Sephadex G-75 column (φ5×90 cm, developing solution: 0.9% saline solution, flow rate: 4 ml/min). Fractions of 15 ml each were collected and active fractions (fraction numbers 49 to 58, 150 ml) were combined. After $\frac{1}{10}$ volume of 1 M Tris-HCl (pH 7.4) was added, the mixture was adsorbed on a DEAE-TOYOPEARL 650M (φ16×300 mm) and eluted with a concentration gradient of NaCl (0.15 M for 200 minutes, from 0.15 M to 0.4 M for 400 minutes, flow rate: 0.5 ml/min). The active fractions (570 to 630 minutes, 30 ml) were collected to obtain purified botrocetin.

Fixed platelets were prepared as follows. To human platelet-rich plasma (PRP) obtained by centrifuging fresh blood collected from a healthy human subject, to which $\frac{1}{10}$ volume of 3.8% sodium citrate was added, at 900 rpm for 15 minutes, an equal volume of a 0.15 M sodium chloride aqueous solution in 20 mM phosphate buffer (pH 7.4) dissolving 2% paraformaldehyde was added, and the mixture was left overnight at 4° C. Then, platelets were collected by centrifugation and washed twice with 0.15 M sodium chloride aqueous solution in 20 mM phosphate buffer (pH 7.4). After the washing, fixed platelets were suspended in the same solution and stored.

To each well of a 96-well filter plate (0.45 µM, Millipore Multiscreen HV, Millipore) for performing an assay, 1% BSA/TBS (100 µl) was added and it was left for several hours to block the filter beforehand. To each well, 20 µl of a suspension obtained by diluting the aforementioned fixed platelet suspension 10-fold with TBS and 5 µl of a test sample and further 20 µl of $^{125}$I labeled vWF solution (about 800,000 cpm) containing 0.8 µg/ml of the aforementioned botrocetin or 2.4 mg/ml ristocetin (Sigma) were added and it was left for 30 minutes. The solution in the wells were filtered by suction, and then TBS (100 µl) containing 0.05% Tween-20 was added and it was further washed by suction. The filter was removed from the 96-well filter plate after the washing by using a punch (Millipore, Model No. MAPK 8960B) and divided into 6-ml volume polystyrene tubes, and a radiation dose of $^{125}$I was measured by using Packard Multi Prias 4.

Figure 8A:
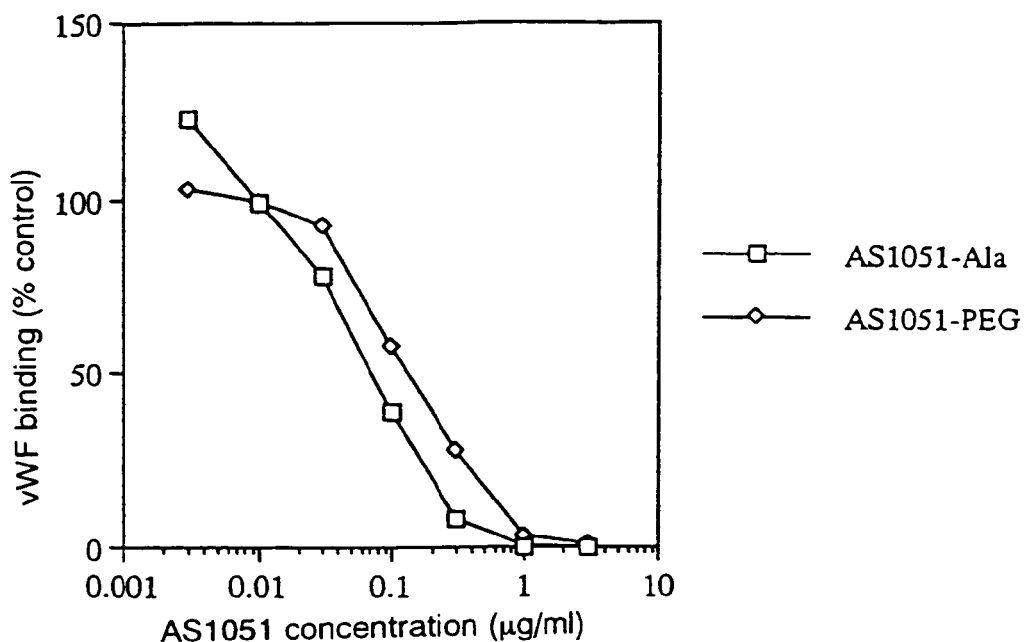
In FIG. 8a the results are shown for restocetin-induced vWF binding, while in FIG. 8b the results are shown for botrocetin-induced vWF binding.
Figure 8B:
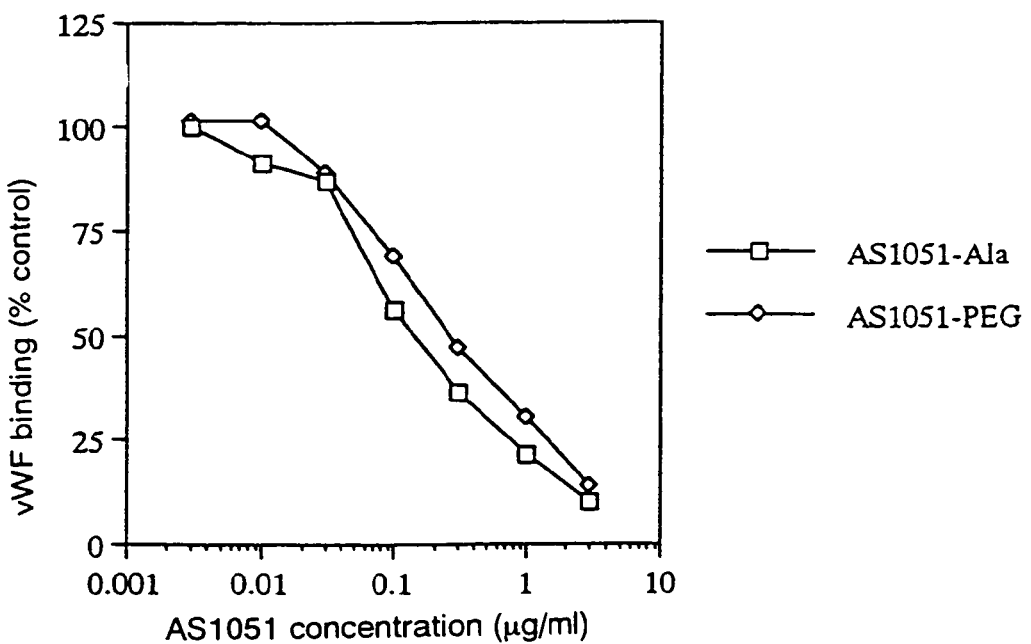
FIG. 8 shows activities of AS1051-Ala and AS1051-PEG for inhibiting binding of fixed platelets and vWF.

As a result, as shown in FIG. 8, it was confirmed that the activity of AS1051-PEG for inhibiting binding of vWF to immobilized platelets induced by ristocetin and botrocetin was slightly weaker than that of AS1051-Ala, but almost comparable. Further, AS1051-PEG20000 also had almost the same activity as that of AS1051-PEG in either method.

Example 8

Antigenicity Test of AS1051-PEG in Guinea Pig

Figure 9:
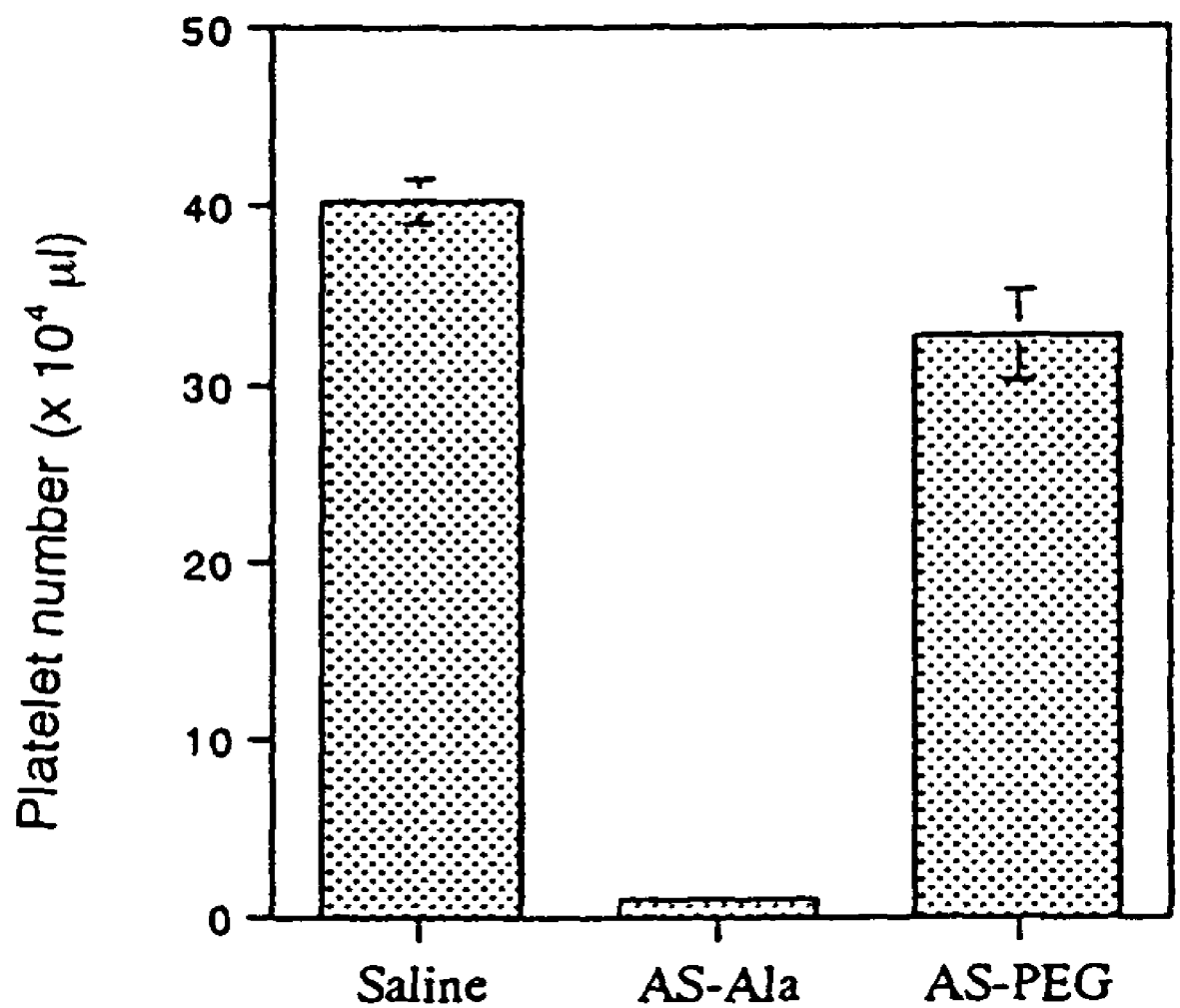
FIG. 9 shows the number of platelets in guinea pigs after repetitive administrations of AS1051-Ala and AS1051-PEG.

A test for comparing antigenicity in a guinea pig of the polyethylene-glycolated protein described in Example 6 (1) (AS1051-PEG, PEG moiety had a molecular weight of 5000) and that of AS1051-Ala was performed in the same manner as in the method described in Example 4. The protein was quantified in the same manner as in Example 4 for AS1051-Ala. As for AS1051-PEG, the protein was quantified by comparing the elution peak area at 280 nm obtained by reverse phase HPLC with that of AS1051-Ala. The same area was defined as the same amount of proteins. The doses of AS1051-Ala and AS1051-PEG were 200 µg/kg at any administration. The subjects were divided into three groups of AS-Ala group (three times of preliminary administration of AS1051-Ala and final administration of AS1051-Ala), AS-PEG group (three times of preliminary administration of AS1051-PEG and final administration of AS1051-PEG) and saline group (three times of preliminary administration of physiological saline and final administration of physiological saline), at n=4 for each group (n=3 in AS-PEG group) to perform an experiment. As a result, as shown in FIG. 9, no difference in the number of platelets was observed between the AS-PEG group and the saline group, and a significant decrease of platelets was observed in the AS-Ala group compared with the AS-PEG group and the saline group. Since it is considered that this decrease of platelets is attributable to antigenicity as shown in Example 4, these results clearly show that AS1051-PEG had decreased antigenicity compared with AS1051-Ala.

INDUSTRIAL APPLICABILITY

According to the present invention, a peptide originating from an oligomeric protein can be produced in a form having more excellent solubility and stability as well as decreased antigenicity compared with those obtained by conventional methods.

What is claimed is:

1. A method for purifying the α-subunit originating from an oligomeric protein *Crotalus horridus horridus* B (CHH-B) having disulfide bonds within a subunit and between subunits, which comprises:
   (a) refolding the α-subunit by denaturing the oligomeric protein or its α-subunit in a solution comprising a reducing agent and a protein-denaturing agent and removing the reducing agent and the denaturing agent from the solution in the presence of polyoxyalkyl polyether having a functional group that reacts with a thiol group to allow the α-subunit to bind to the polyoxyalkyl polyether via the reaction between the thiol group of the α-subunit and the functional group of the polyoxyalkyl polyether that reacts with a thiol group; and
   (b) isolating the α-subunit of the *Crotalus horridus horridus* B (CHH-B) that is bonded to the polyoxyalkyl polyether from the solution.

2. The method according to claim 1, wherein the α-subunit isolated in (b) has decreased antigenicity.

3. The method according to claim 1, wherein the polyoxyalkyl polyether having the functional group that reacts with the thiol group is polyethylene glycol having a maleimide group.

4. The method according to claim 1, wherein the α-subunit originating from the oligomeric protein is a recombinant protein.

5. The method according to claim 1, wherein a physiological activity of the oligomeric protein arises from the α-subunit constituting the oligomeric protein, and the subunit peptide bonded to polyoxyalkyl polyether has the physiological activity.

6. The method according to claim 1, wherein the α-subunit bonded to polyoxyalkyl polyether has an activity of inhibiting a physiological activity of the oligomeric protein.

7. The method according to claim 1, wherein the polyoxyalkyl polyether is bonded to a cysteine residue of the α-subunit that is originally involved in formation of a disulfide bond between subunits in the oligomeric protein.

8. The method according to claim 1, wherein the α-subunit bonded to polyoxyalkyl polyether has a disulfide bond identical to a disulfide bond within the subunit in the oligomeric protein.

* * * * *

SEQUENCE LISTING

<160> NUMBER OF SEQ ID NOS: 10

<210> SEQ ID NO 1
<211> LENGTH: 126
<212> TYPE: PRT
<213> ORGANISM: Crotalus horridus horridus

<400> SEQUENCE: 1

Asp Leu Glu Cys Pro Ser Gly Trp Ser Ser Tyr Asp Arg Tyr Cys Tyr
1               5                   10                  15

Lys Pro Phe Lys Gln Glu Met Thr Trp Ala Asp Ala Gln Arg Phe Cys
            20                  25                  30

Ser Glu Gln Ala Lys Gly Gly His Leu Leu Ser Val Glu Thr Ala Leu
        35                  40                  45

Glu Ala Ser Phe Val Asp Asn Val Leu Tyr Ala Asn Lys Glu Tyr Leu
    50                  55                  60

Thr Arg Tyr Ile Trp Ile Gly Leu Arg Val Gln Asn Lys Gly Gln Pro
65                  70                  75                  80

Cys Ser Ser Ile Ser Tyr Glu Asn Leu Val Asp Pro Phe Glu Cys Phe
                85                  90                  95

Met Val Ser Arg Asp Thr Arg Leu Arg Glu Trp Phe Lys Val Asp Cys
            100                 105                 110

Glu Gln Gln His Ser Phe Ile Cys Lys Phe Thr Arg Pro Arg
            115                 120                 125

<210> SEQ ID NO 2
<211> LENGTH: 17
<212> TYPE: DNA
<213> ORGANISM: ARTIFICIAL SEQUENCE
<220> FEATURE:
<223> OTHER INFORMATION: SYNTHETIC DNA
<221> NAME/KEY: misc_feature
<222> LOCATION: (12)..(12)
<223> OTHER INFORMATION: n=a, g, c or t

<400> SEQUENCE: 2
cargaratga cntgggc                                                  17

<210> SEQ ID NO 3
<211> LENGTH: 17
<212> TYPE: DNA
<213> ORGANISM: ARTIFICIAL SEQUENCE
<220> FEATURE:
<223> OTHER INFORMATION: SYNTHETIC DNA
<221> NAME/KEY: misc_feature
<222> LOCATION: (3)..(3)
<223> OTHER INFORMATION: n=a, g, c or t

<400> SEQUENCE: 3
tcnacyttra accaytc                                                  17

<210> SEQ ID NO 4
<211> LENGTH: 272

```
-continued

<212> TYPE: DNA
<213> ORGANISM: Crotalus horridus horridus

<400> SEQUENCE: 4
caggagatga cttgggccga tgcagagagg ttctgctcgg agcaggcgaa gggcgggcat      60
ctcctctctg tcgaaaccgc cctagaagca tcctttgtgg acaatgtgct ctatgcgaac     120
aaagagtacc tcacacgtta tatctggatt ggactgaggg ttcaaaacaa aggacagcca     180
tgctccagca tcagttatga gaacctggtt gacccatttg aatgttttat ggtgagcaga     240
gacacaaggc ttcgtgagtg gttcaaagtc ga                                   272

<210> SEQ ID NO 5
<211> LENGTH: 690
<212> TYPE: DNA
<213> ORGANISM: Crotalus horridus horridus
<220> FEATURE:
<221> NAME/KEY: CDS
<222> LOCATION: (66)..(512)
<223> OTHER INFORMATION:

<400> SEQUENCE: 5
ctgagcagac ttgctacctg tggaggccga ggaacagttc tctctgcagg gaaggaaaga      60 acgcc atg ggg cga ttc atc ttc gtg agc ttc aac ttg ctg gtc gtg ttc    110
      Met Gly Arg Phe Ile Phe Val Ser Phe Asn Leu Leu Val Val Phe
       1               5                  10                  15 ctc tcc cta agt gga act cta gct gat ttg gaa tgt ccc tcc ggt tgg      158
Leu Ser Leu Ser Gly Thr Leu Ala Asp Leu Glu Cys Pro Ser Gly Trp
             20                  25                  30 tct tcc tat gat cgg tat tgc tac aag ccc ttc aaa caa gag atg acc      206
Ser Ser Tyr Asp Arg Tyr Cys Tyr Lys Pro Phe Lys Gln Glu Met Thr
         35                  40                  45 tgg gcc gat gca gag agg ttc tgc tcg gag cag gcg aag ggc ggg cat      254
Trp Ala Asp Ala Glu Arg Phe Cys Ser Glu Gln Ala Lys Gly Gly His
     50                  55                  60 ctc ctc tct gtc gaa acc gcc cta gaa gca tcc ttt gtg gac aat gtg      302
Leu Leu Ser Val Glu Thr Ala Leu Glu Ala Ser Phe Val Asp Asn Val
 65                  70                  75 ctc tat gcg aac aaa gag tac ctc aca cgt tat atc tgg att gga ctg      350
Leu Tyr Ala Asn Lys Glu Tyr Leu Thr Arg Tyr Ile Trp Ile Gly Leu
80                  85                  90                  95 agg gtt caa aac aaa gga cag cca tgc tcc agc atc agt tat gag aac      398
Arg Val Gln Asn Lys Gly Gln Pro Cys Ser Ser Ile Ser Tyr Glu Asn
                100                 105                 110 ctg gtt gac cca ttt gaa tgt ttt atg gtg agc aga gac aca agg ctt      446
Leu Val Asp Pro Phe Glu Cys Phe Met Val Ser Arg Asp Thr Arg Leu
             115                 120                 125 cgt gag tgg ttt aaa gtt gac tgt gaa caa caa cat tct ttc ata tgc      494
Arg Glu Trp Phe Lys Val Asp Cys Glu Gln Gln His Ser Phe Ile Cys
         130                 135                 140 aag ttc acg cga cca cgt taagatccgg ctgtgtaag tctggagaag              542
Lys Phe Thr Arg Pro Arg
         145 caaggaagcc ccccacctct ccccaccccc caccttccgc aatctctgct cttccccctt     602 tgctcagtgg atgctctctg tagccggatc tgggttttct gctccagatg ggtcagaaga    662 tccaataaat tctgcctacc caaaaaaa                                        690

<210> SEQ ID NO 6
<211> LENGTH: 149
<212> TYPE: PRT
```

-continued

<213> ORGANISM: Crotalus horridus horridus

<400> SEQUENCE: 6

```
Met Gly Arg Phe Ile Phe Val Ser Phe Asn Leu Leu Val Val Phe Leu
1               5                   10                  15

Ser Leu Ser Gly Thr Leu Ala Asp Leu Glu Cys Pro Ser Gly Trp Ser
            20                  25                  30

Ser Tyr Asp Arg Tyr Cys Tyr Lys Pro Phe Lys Gln Glu Met Thr Trp
        35                  40                  45

Ala Asp Ala Glu Arg Phe Cys Ser Glu Gln Ala Lys Gly Gly His Leu
    50                  55                  60

Leu Ser Val Glu Thr Ala Leu Glu Ala Ser Phe Val Asp Asn Val Leu
65                  70                  75                  80

Tyr Ala Asn Lys Glu Tyr Leu Thr Arg Tyr Ile Trp Ile Gly Leu Arg
                85                  90                  95

Val Gln Asn Lys Gly Gln Pro Cys Ser Ser Ile Ser Tyr Glu Asn Leu
            100                 105                 110

Val Asp Pro Phe Glu Cys Phe Met Val Ser Arg Asp Thr Arg Leu Arg
        115                 120                 125

Glu Trp Phe Lys Val Asp Cys Glu Gln Gln His Ser Phe Ile Cys Lys
    130                 135                 140

Phe Thr Arg Pro Arg
145
```

<210> SEQ ID NO 7
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 7
attggatcca tggatttgga atgtccctcc 30

<210> SEQ ID NO 8
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 8
aataagctta acgtggtcgc gtgaacttgc 30

<210> SEQ ID NO 9
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 9
gatgctggag gctggctgtc ctttgt 26

<210> SEQ ID NO 10
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 10
ggacagccag cctccagcat cagtta 26